United States Patent [19]
Billig et al.

[11] Patent Number: 5,767,321
[45] Date of Patent: *Jun. 16, 1998

[54] METAL-LIGAND COMPLEX CATALYZED PROCESSES

[75] Inventors: Ernst Billig, Huntington; David Robert Bryant, South Charleston, both of W. Va.

[73] Assignee: Union Carbide Chemicals & Plastics Technology Corporation, Danbury, Conn.

[ * ] Notice: The term of this patent shall not extend beyond the expiration date of Pat. No. 5,741,944.

[21] Appl. No.: 757,740

[22] Filed: Nov. 26, 1996

Related U.S. Application Data

[60] Provisional application Nos. 60/008,289, Dec. 6, 1996, 60/008,763, Dec. 6, 1996, 60/008,284, Dec. 6, 1996 and 60/008,286, Dec. 6, 1996.

[51] Int. Cl.$^6$ ............................................. C07C 45/50
[52] U.S. Cl. ................................. 568/454; 568/451
[58] Field of Search ............................ 568/451, 454

[56] References Cited

U.S. PATENT DOCUMENTS 3,917,661  11/1975  Roy et al. .
5,288,918  2/1994  Maher et al. ........................ 568/454

FOREIGN PATENT DOCUMENTS 0096987  12/1983  European Pat. Off. .

*Primary Examiner*—Gary Geist
*Assistant Examiner*—Sreeni Padmanabhan
*Attorney, Agent, or Firm*—Gerald L. Coon

[57] ABSTRACT

This invention relates to a process which comprises reacting one or more reactants in the presence of a metal-organopolyphosphite ligand complex catalyst to produce a reaction product fluid comprising one or more products, wherein said process is conducted at a free organopolyphosphite ligand concentration sufficient to prevent and/or lessen hydrolytic degradation of the organopolyphosphite ligand and deactivation of the metal-organopolyphosphite ligand complex catalyst.

19 Claims, 1 Drawing Sheet

METAL-LIGAND COMPLEX CATALYZED PROCESSES

This application claims the benefit of provisional U.S. patent application Ser. Nos. 60/008289, 60/008763, 60/008284 and 60/008286, all filed Dec. 6, 1995, and all of which are incorporated herein by reference.

BRIEF SUMMARY OF THE INVENTION

1. Technical Field

This invention relates to improved metal-organopolyphosphite ligand complex catalyzed processes. More particularly this invention relates to the use of free organopolyphosphite ligand at low organopolyphosphite ligand to metal ratios to prevent and/or lessen hydrolytic degradation of the organopolyphosphite ligand and deactivation of the metal-organopolyphosphite ligand complex catalyst of such processes.

2. Background of the Invention

It is known in the art that various products may be produced by reacting one or more reactants in the presence of an metal-organopolyphosphite ligand complex catalyst. However, stabilization of the catalyst and organopolyphosphite ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Likewise degradation of the organophosphite ligand employed during the process can lead to poisoning organophosphite compounds or inhibitors or acidic byproducts that can lower the catalytic activity of the metal catalyst. Moreover, production costs of the product obviously increase when productivity of the catalyst decreases.

For instance, a major cause of organophosphite ligand degradation and catalyst deactivation of metal-organophosphite ligand complex catalyzed hydroformylation processes is due to the hydrolytic instability of the organophosphite ligands. All organophosphites are susceptible to hydrolysis in one degree or another, the rate of hydrolysis of organophosphites in general being dependent on the stereochemical nature of the organophosphite. In general, the bulkier the steric environment around the phosphorus atom, the slower the hydrolysis rate. For example, tertiary triorganophosphites such as triphenylphosphite are more susceptible to hydrolysis than diorganophosphites, such as disclosed in U.S. Pat. No. 4,737,588, and organopolyphosphites such as disclosed in U.S. Pat. Nos. 4,748,261 and 4,769,498. Moreover, all such hydrolysis reactions invariably produce phosphorus acidic compounds which catalyze the hydrolysis reactions. For example, the hydrolysis of a tertiary organophosphite produces a phosphonic acid diester, which is hydrolyzable to a phosphonic acid monoester, which in turn is hydrolyzable to $H_3PO_3$ acid. Moreover, hydrolysis of the ancillary products of side reactions, such as between a phosphonic acid diester and the aldehyde or between certain organophosphite ligands and an aldehyde, can lead to production of undesirable strong aldehyde acids, e.g., $n-C_3H_7CH(OH)P(O)(OH)_2$.

Indeed even highly desirable sterically-hindered organo-bisphosphites which are not very hydrolyzable can react with the aldehyde product to form poisoning organophosphites, e.g., organomonophosphites, which are not only catalytic inhibitors, but far more susceptible to hydrolysis and the formation of such aldehyde acid byproducts, e.g., hydroxy alkyl phosphonic acids, as shown, for example, in U.S. Pat. Nos. 5,288,918 and 5,364,950. Further, the hydrolysis of organophosphite ligands may be considered as being autocatalytic in view of the production of such phosphorus acidic compounds, e.g., $H_3PO_3$, aldehyde acids such as hydroxy alkyl phosphonic acids, $H_3PO_4$ and the like, and if left unchecked the catalyst system of the continuous liquid recycle hydroformylation process will become more and more acidic in time. Thus in time the eventual build-up of an unacceptable amount of such phosphorus acidic materials can cause the total destruction of the organophosphite present, thereby rendering the hydroformylation catalyst totally ineffective (deactivated) and the valuable rhodium metal susceptible to loss, e.g., due to precipitation and/or depositing on the walls of the reactor. Accordingly, a successful method for preventing and/or lessening such hydrolytic degradation of the organophosphite ligand and deactivation of the catalyst would be highly desirable to the art.

DISCLOSURE OF THE INVENTION

It has now been discovered that free organopolyphosphite ligand at low organopolyphosphite ligand to metal ratios may be employed to effectively prevent and/or lessen hydrolytic degradation of the organopolyphosphite ligand and deactivation of metal-organopolyphosphite ligand complex catalysts that may occur over the course of time during processes which employ metal-organopolyphosphite ligand complex catalysts. It has been surprisingly discovered that by reducing the amount of free organopolyphosphite ligand to preferred levels of from zero to about 4 moles per mole of metal, adventitious hydrolysis can be reduced so that the processes can be operated below the threshold for autocatalytic hydrolysis of organopolyphosphite ligand and at a residence time in the reactors sufficient to prevent and/or lessen hydrolytic degradation of the organopolyphosphite ligand and deactivation of the metal-organopolyphosphite ligand complex catalyst. The processes of this invention can be operated at high raw material efficiencies, e.g., high conversion of olefinic unsaturated compounds.

This invention relates in part to a process which comprises reacting one or more reactants in the presence of a metal-organopolyphosphite ligand complex catalyst to produce a reaction product fluid comprising one or more products, wherein said process is conducted at a free organopolyphosphite ligand concentration sufficient to prevent and/or lessen hydrolytic degradation of the organopolyphosphite ligand and deactivation of the metal-organopolyphosphite ligand complex catalyst.

This invention also relates in part to a process which comprises reacting one or more reactants in the presence of a metal-organopolyphosphite ligand complex catalyst to produce a reaction product fluid comprising one or more products, wherein said process is conducted (a) at a free organopolyphosphite ligand concentration sufficient to prevent and/or lessen hydrolytic degradation of the organopolyphosphite ligand and deactivation of the metal-organopolyphosphite ligand complex catalyst and (b) at a reaction zone and/or separator zone residence time sufficient to prevent and/or lessen hydrolytic degradation of the organopolyphosphite ligand and deactivation of the metal-organopolyphosphite ligand complex catalyst.

This invention further relates in part to an improved process for producing one or more products which comprises (i) reacting in at least one reaction zone one or more reactants in the presence of a metal-organopolyphosphite ligand complex catalyst to produce a reaction product fluid comprising one or more products and (ii) separating in at least one separation zone or in said at least one reaction zone the one or more products from said reaction product fluid, the improvement comprising preventing and/or lessening hydrolytic degradation of the organopolyphosphite ligand and deactivation of the metal-organopolyphosphite ligand complex catalyst by conducting said process (a) at a free organopolyphosphite ligand concentration sufficient to prevent and/or lessen hydrolytic degradation of the organopolyphosphite ligand and deactivation of the metal-organopolyphosphite ligand complex catalyst, and (b) at a reaction zone and/or separator zone residence time sufficient to prevent and/or lessen hydrolytic degradation of the organopolyphosphite ligand and deactivation of the metal-organopolyphosphite ligand complex catalyst; and by treating in at least one acid removal zone at least a portion of said reaction product fluid derived from said process and which also contains phosphorus acidic compounds formed during said process with an acid removal substance sufficient to remove at least some amount of the phosphorus acidic compounds from said reaction product fluid.

This invention yet further relates in part to an improved process for producing one or more products which comprises (i) reacting in at least one reaction zone one or more reactants in the presence of a metal-organopolyphosphite ligand complex catalyst to produce a reaction product fluid comprising one or more products and (ii) separating in at least one separation zone or in said at least one reaction zone the one or more products from said reaction product fluid, the improvement comprising preventing and/or lessening hydrolytic degradation of the organopolyphosphite ligand and deactivation of the metal-organopolyphosphite ligand complex catalyst by conducting said process (a) at a free organopolyphosphite ligand concentration sufficient to prevent and/or lessen hydrolytic degradation of the organopolyphosphite ligand and deactivation of the metal-organopolyphosphite ligand complex catalyst, and (b) at a reaction zone and/or separator zone residence time sufficient to prevent and/or lessen hydrolytic degradation of the organopolyphosphite ligand and deactivation of the metal-organopolyphosphite ligand complex catalyst; and by removing phosphorus acidic compounds from said reaction product fluid derived from said process by (a) withdrawing from said at least one reaction zone or said at least one separation zone at least a portion of a reaction product fluid derived from said process and which also contains phosphorus acidic compounds formed during said process, (b) treating in at least one acid removal zone at least a portion of the withdrawn reaction product fluid derived from said process and which also contains phosphorus acidic compounds formed during said process with an acid removal substance sufficient to remove at least some amount of the phosphorus acidic compounds from said reaction product fluid, and (c) returning the treated reaction product fluid to said at least one reaction zone or said at least one separation zone.

DETAILED DESCRIPTION

General Processes

Figure 1:
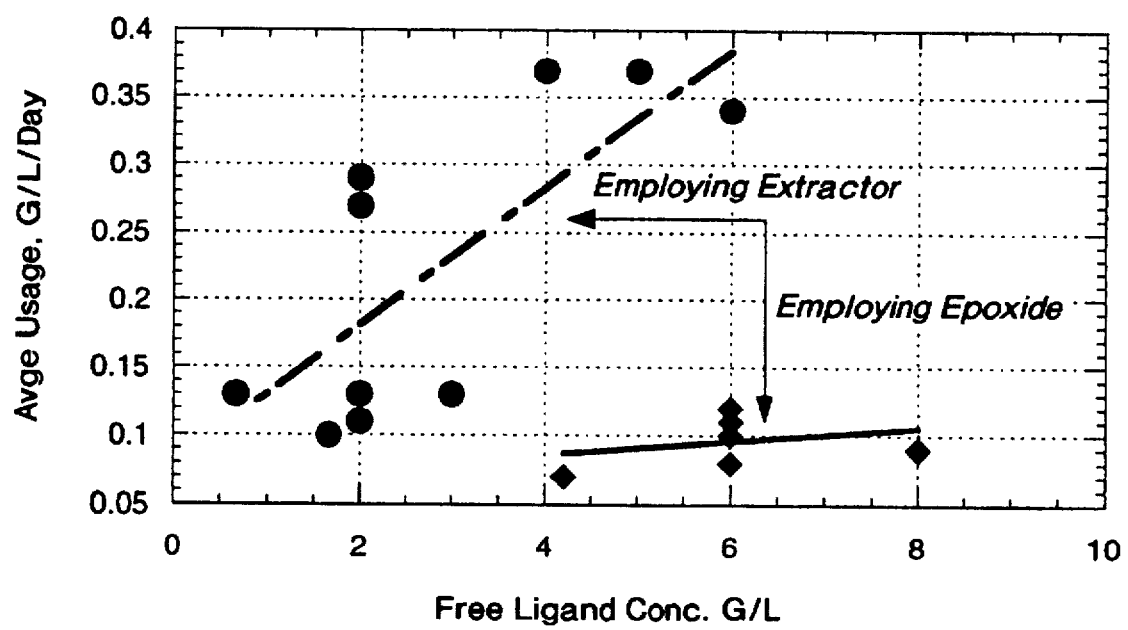
FIG. 1 is a graphical representation of free ligand concentration (grams/liter) versus average ligand usage (grams/liter/day) based on the experimental data set out in Table A herein.

The processes of this invention may be asymmetric or non-asymmetric, the preferred processes being non-asymmetric, and may be conducted in any continuous or semi-continuous fashion and may involve any catalyst liquid and/or gas recycle operation desired. The particular processes for producing products from one or more reactants, as well as the reaction conditions and ingredients of the processes are not critical features of this invention. The processing techniques of this invention may correspond to any of the known processing techniques heretofore employed in conventional processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion. As used herein, the term "reaction product fluid" is contemplated to include, but not limited to, a reaction mixture containing an amount of any one or more of the following: (a) a metal-organopolyphosphite ligand complex catalyst, (b) free organopolyphosphite ligand, (c) one or more phosphorus acidic compounds formed in the reaction, (d) aldehyde product formed in the reaction, (e) unreacted reactants, and (f) an organic solubilizing agent for said metal-organopolyphosphite ligand complex catalyst and said free organopolyphosphite ligand. The reaction product fluid encompasses, but is not limited to, (a) the reaction medium in the reaction zone, (b) the reaction medium stream on its way to the separation zone, (c) the reaction medium in the separation zone, (d) the recycle stream between the separation zone and the reaction zone, (e) the reaction medium withdrawn from the reaction zone or separation zone for treatment in the acid removal zone, (f) the withdrawn reaction medium treated in the acid removal zone, (g) the treated reaction medium returned to the reaction zone or separation zone, and (h) reaction medium in external cooler.

This invention encompasses the carrying out of known conventional syntheses in a conventional fashion employing a metal-organopolyphosphite ligand complex catalyst and free organopolyphosphite ligand at low organopolyphosphite ligand to metal ratios to effectively prevent and/or lessen hydrolytic degradation of the organopolyphosphite ligand and deactivation of metal-organopolyphosphite ligand complex catalysts that may occur over the course of time during processes which employ metal-organopolyphosphite ligand complex catalysts.

Illustrative processes include, for example, hydroformylation, hydroacylation (intramolecular and intermolecular), hydrocyanation, hydroamidation, hydroesterification, aminolysis, alcoholysis, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-organopolyphosphite ligand complex catalyst. The most preferred processes include hydroformylation, hydrocyanation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organopolyphosphite ligand complex catalyst described herein. Alternatively, hydroxyaldehydes can be prepared by reacting an epoxide, carbon monoxide and hydrogen under hydroformylation conditions in the presence of a metal-organopolyphosphite ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-organopolyphosphite ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organopolyphosphite ligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-organopolyphosphite ligand complex catalyst described herein. A preferred hydrocyanation process involves reacting a nonconjugated acyclic aliphatic monoolefin, a monoolefin conjugated to an ester group, e.g., methyl pent-2-eneoate, or a monoolefin conjugated to a nitrile group, e.g., 3-pentenenitrile, with a source of hydrogen cyanide in the presence of a catalyst precursor composition comprising zero-valent nickel and a bidentate phosphite ligand to produce a terminal organonitrile, e.g., adiponitrile, alkyl 5-cyanovalerate or 3-(perfluoroalkyl) propionitrile. Preferably, the reaction is carried out in the presence of a Lewis acid promoter. Illustrative hydrocyanation processes are disclosed in U.S. Pat. No. 5,523,453 and WO 95/14659, the disclosures of which are incorporated herein by reference.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organopolyphosphite ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organopolyphosphite ligand complex catalyst described herein.

Aminolysis can be carried out in accordance with conventional procedures known in the art. For example, amines can be prepared by reacting an olefin with a primary or secondary amine under aminolysis conditions in the presence of a metal-organopolyphosphite ligand complex catalyst described herein.

Alcoholysis can be carried out in accordance with conventional procedures known in the art. For example, ethers can be prepared by reacting an olefin with an alcohol under alcoholysis conditions in the presence of a metal-organopolyphosphite ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organopolyphosphite ligand complex catalyst described herein.

Isomerization can be carried out in accordance with conventional procedures known in the art. For example, allylic alcohols can be isomerized under isomerization conditions to produce aldehydes in the presence of a metal-organopolyphosphite ligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-organopolyphosphite ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, intermolecular hydroacylation, hydrocyanation, hydroamidation, hydroesterification, aminolysis, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-organopolyphosphite ligand complex catalysts employable in the processes encompassed by this invention are known in the art and include those disclosed in the below mentioned patents. In general such catalysts may be preformed or formed in situ as described in such references and consist essentially of metal in complex combination with an organopolyphosphite ligand or an organophosphorus ligand as the case may be. The active species may also contain carbon monoxide and/or hydrogen directly bonded to the metal.

The catalysts useful in the processes of this invention include a metal-organopolyphosphite ligand complex catalyst, which can be optically active or non-optically active. The permissible metals which make up the metal-organopolyphosphite ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 6 metals selected from chromium (Cr), molybdenum (Mo), tungsten (W) and mixtures thereof Mixtures of metals from Groups 6, 8, 9 and 10 may also be used in this invention.

The permissible organopolyphosphite ligands which make up the metal-organopolyphosphite ligand complexes and free organopolyphosphite ligand include di-, tri- and higher polyorganophosphites. Mixtures of such ligands may be employed if desired in the metal-organopolyphosphite ligand complex catalyst and/or any free organopolyphosphite ligand and such mixtures may be the same or different. This invention is not intended to be limited in any manner by the permissible organopolyphosphite ligands or mixtures thereof. It is to be noted that the successful practice of this invention does not depend and is not predicated on the exact structure of the metal-organopolyphosphite ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organopolyphosphite ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organopolyphosphite ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and RP(O)(OH)O (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organopolyphosphite ligand complex catalyzed reactions that the active catalysts be free of halogen and sulfur directly bonded to the metal, although such may not be absolutely necessary.

The number of available coordination sites on such metals is well known in the art. Thus the catalytic species may comprise a complex catalyst mixture, in their monomeric, dimeric or higher nuclearity forms, which are preferably characterized by at least one organopolyphosphite-containing molecule complexed per one molecule of metal, e.g., rhodium. For instance, it is considered that the catalytic species of the preferred catalyst employed in a hydroformylation reaction may be complexed with carbon monoxide and hydrogen in addition to the organopolyphosphite ligands in view of the carbon monoxide and hydrogen gas employed by the hydroformylation reaction.

The organopolyphosphites that may serve as the ligand of the metal-organopolyphosphite ligand complex catalyst and/or free ligand of the processes and reaction product fluids of this invention may be of the achiral (optically inactive) or chiral (optically active) type and are well known in the art. Achiral organopolyphosphites are preferred.

Among the organopolyphosphites that may serve as the ligand of the metal-organopolyphosphite ligand complex catalyst containing reaction product fluids of this invention and/or any free organopolyphosphite ligand of the process that might also be present in said reaction product fluids are organopolyphosphite compounds described below. Such organopolyphosphite ligands employable in this invention and/or methods for their preparation are well known in the art.

Representative organopolyphosphites contain two or more tertiary (trivalent) phosphorus atoms and may include those having the formula:

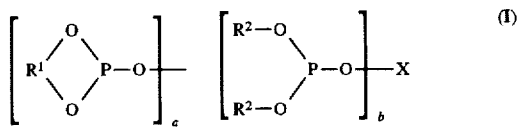

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^1$ radical may be the same or different, and when b has a value of 1 or more, each $R^2$ radical may be the same or different.

Representative n-valent (preferably divalent) hydrocarbon bridging radicals represented by X and representative divalent organic radicals represented by $R^1$ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein each y is the same or different and is a value of 0 or 1, Q represents a divalent bridging group selected from —$C(R^3)_2$—, —O—, —S—, —$NR^4$—, $Si(R^5)_2$—and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, e.g., an alkyl radical having 1 to 4 carbon atoms; each $R^5$ is the same or different and represents hydrogen or an alkyl radical, and m is a value of 0 or 1. The more preferred acyclic radicals represented by X and $R^1$ above are divalent alkylene radicals, while the more preferred aromatic radicals represented by X and $R^1$ above are divalent arylene and bisarylene radicals, such as disclosed more fully, for example, in U.S. Pat. Nos. 4,769,498; 4,774,361; 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative preferred monovalent hydrocarbon radicals represented by each $R^2$ radical above include alkyl and aromatic radicals.

Illustrative preferred organopolyphosphites may include bisphosphites such as those of Formulas (II) to (IV) below:

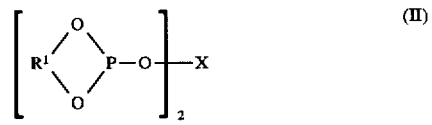

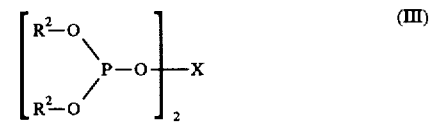

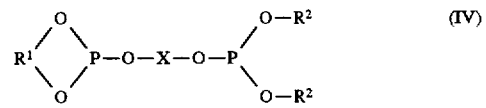

wherein each $R^1$, $R^2$ and X of Formulas (II) to (IV) are the same as defined above for Formula (I). Preferably each $R^1$ and X represents a divalent hydrocarbon radical selected from alkylene, arylene, arylene-alkylene-arylene, and bisarylene, while each R² radical represents a monovalent hydrocarbon radical selected from alkyl and aryl radicals. Organopolyphosphite ligands of such Formulas (II) to (IV) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following Formulas (V) to (VII):

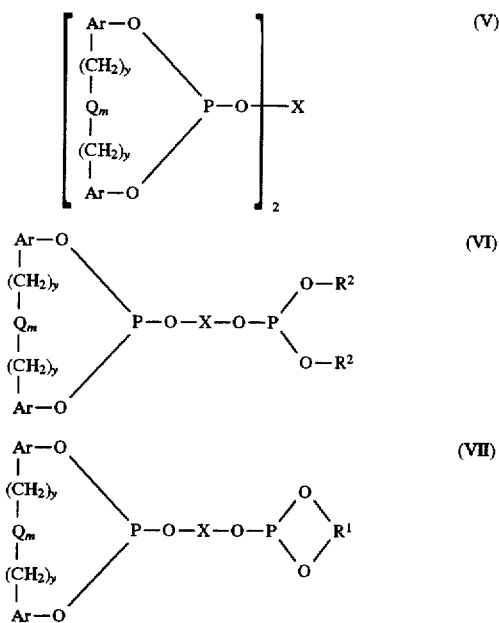

wherein Q R¹, R², X, m, and y are as defined above, and each Ar is the same or different and represents a substituted or unsubstituted aryl radical. Most preferably X represents a divalent aryl-(CH₂)ᵧ—(Q)ₘ—(CH₂)ᵧ-aryl radical wherein each y individually has a value of 0 or 1; m has a value of 0 or 1 and Q is —O—, —S— or —C(R³)₂ where each R³ is the same or different and represents hydrogen or a methyl radical. More preferably each alkyl radical of the above defined R² groups may contain from 1 to 24 carbon atoms and each aryl radical of the above-defined Ar, X, R¹ and R² groups of the above Formulas (V) to (VII) may contain from 6 to 18 carbon atoms and said radicals may be the same or different, while the preferred alkylene radicals of X may contain from 2 to 18 carbon atoms and the preferred alkylene radicals of R¹ may contain from 5 to 18 carbon atoms. In addition, preferably the divalent Ar radicals and divalent aryl radicals of X of the above formulas are phenylene radicals in which the bridging group represented by —(CH₂)ᵧ—(Q)ₘ—(CH₂)ᵧ— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organopolyphosphite in the above Formulas (I) to (VII) may be an ionic phosphite, i.e., may contain one or more ionic moieties selected from the group consisting of:

SO₃M wherein M represents inorganic or organic cation,

PO₃M wherein M represents inorganic or organic cation. N(R⁶)₃X¹ wherein each R⁶ is the same or different and represents a hydrocarbon radical containing from 1 to 30 carbon atoms, e.g., alkyl, aryl, alkaryl, aralkyl, and cycloalkyl radicals, and X¹ represents inorganic or organic anion.

CO₂M wherein M represents inorganic or organic cation, as described, for example, in U.S. Pat. Nos. 5,059,710; 5,113,022 5,114,473; 5,449,653; and European Patent Application Publication No. 435,084, the disclosures of which are incorporated herein by reference. Thus, if desired, such organopolyphosphite ligands may contain from 1 to 3 such ionic moieties, while it is preferred that only one such ionic moiety be substituted on any given aryl moiety in the organopolyphosphite ligand when the ligand contains more than one such ionic moiety. As suitable counter-ions, M and X¹, for the anionic moieties of the ionic organopolyphosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation and quaternary ammonium cations, phosphonium cations, arsonium cations and iminium cations. Suitable anionic atoms of radicals include, for example, sulfate, carbonate, phosphate, chloride, acetate, oxalate and the like.

Of course any of the R¹, R², X, Q and Ar radicals of such non-ionic and ionic organopolyphosphites of Formulas (I) to (VII) above may be substituted if desired, with any suitable substituent containing from 1 to 30 carbon atoms that does not unduly adversely affect the desired result of the process of this invention. Substituents that may be on said radicals in addition of course to corresponding hydrocarbon radicals such as alkyl, aryl, aralkyl, alkaryl and cyclohexyl substituents, may include for example silyl radicals such as —Si(R⁷)₃; amino radicals such as —N(R⁷)₂; phosphine radicals such as -aryl-P(R⁷)₂; acyl radicals such as —C(O)R⁷ acyloxy radicals such as —OC(O)R⁷; amido radicals such as —CON(R⁷)₂ and —N(R⁷)COR⁷; sulfonyl radicals such as —SO₂R⁷, alkoxy radicals such as —OR⁷; sulfinyl radicals such as —SOR⁷, sulfenyl radicals such as —SR⁷, phosphonyl radicals such as —P(O)(R⁷)₂, as well as halogen, nitro, cyano, trifluoromethyl, hydroxy radicals, and the like, wherein each R⁷ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N(R⁷)₂ each R⁷ taken together can also represent a divalent bridging group that forms a heterocyclic radical with the nitrogen atom, and in amido substituents such as —C(O)N(R⁷)₂ and —N(R⁷)COR⁷ each R⁷ bonded to N can also be hydrogen. Of course it is to be understood that any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH₂CH₂OCH₃, —O(CH₂CH₂)₂OCH₃, —O(CH₂CH₂)₃OCH₃, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$—P(O)CH$_3$(C$_6$H$_5$), —P(O)(H)(C$_6$H5), and the like.

Specific illustrative examples of such organobisphosphite ligands include the following:

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

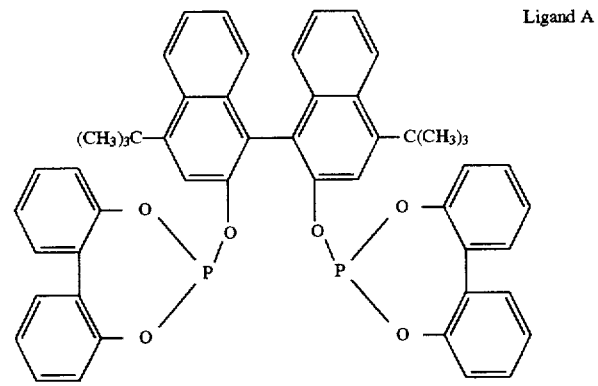

Ligand A 6,6'-[[3,3'-bis(1,1-dimethylethy)-5,5'-dimethoxy-[1,1'-biphenyl]-2,2'-diyl]bis(oxy)]bis-dibenzo[d,f][1,3,2] dioxaphosphepin having the formula:

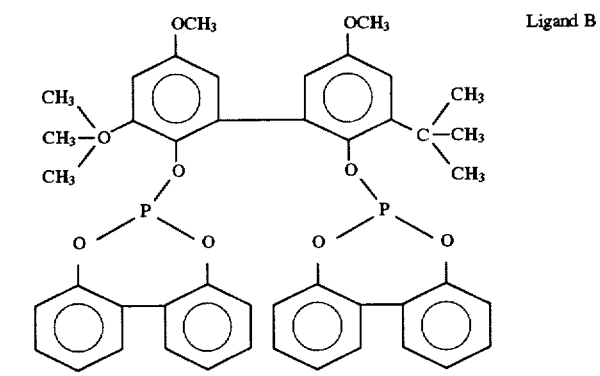

Ligand B 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

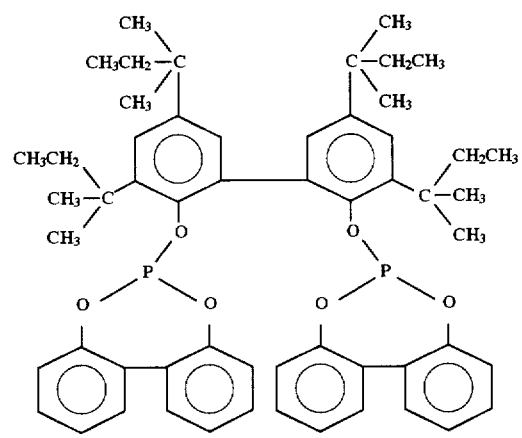

Ligand C 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

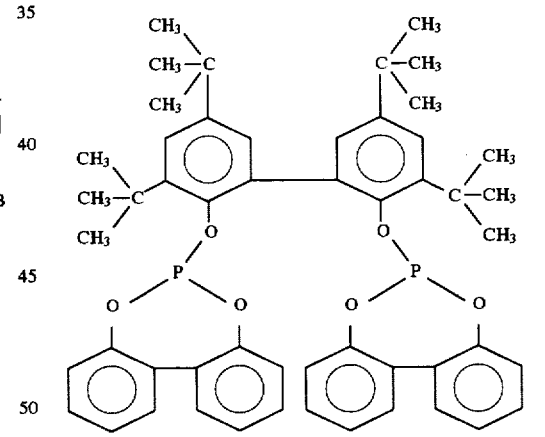

Ligand D (2R,4R)-di[2,2'-(3,3',5,5'-tetrakis-tert-amyl-1,1'-biphenyl)]-2,4-pentyldiphosphite having the formula:

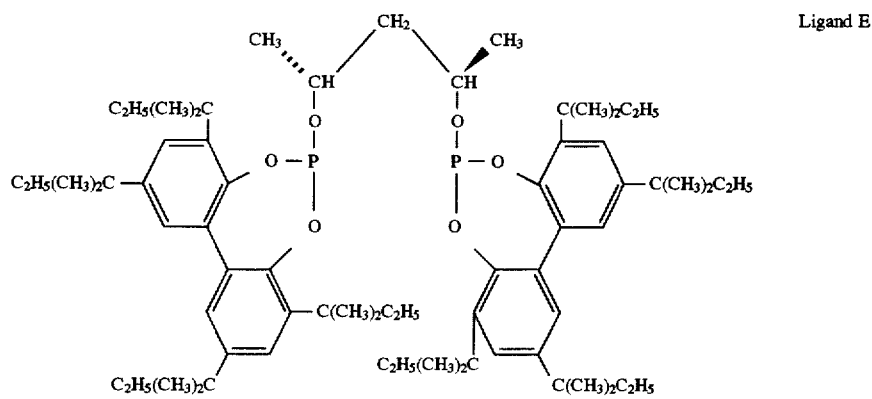
Ligand E
(2R,4R)-di[2,2'-(3,3',5,5'-tetrakis-tert-butyl-1,1'-biphenyl)]-2,4-pentyldiphosphite having the formula:
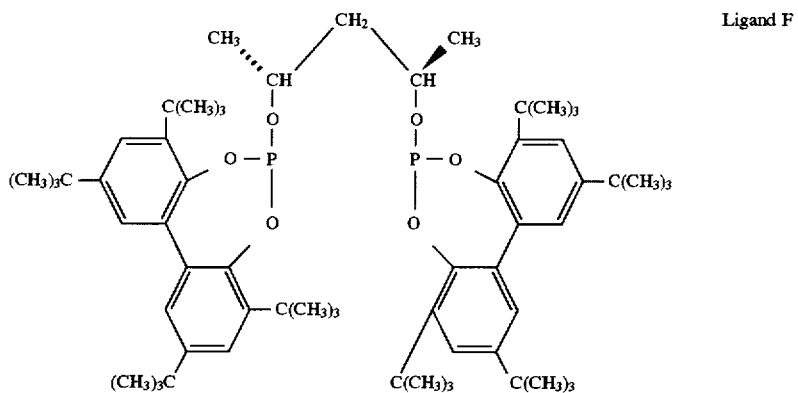
Ligand F
(2R,4R)-di[2,2'-(3,3'-di-amyl-5,5'-dimethoxy-1,1'-biphenyl)]-2,4-pentyldiphosphite having the formula:
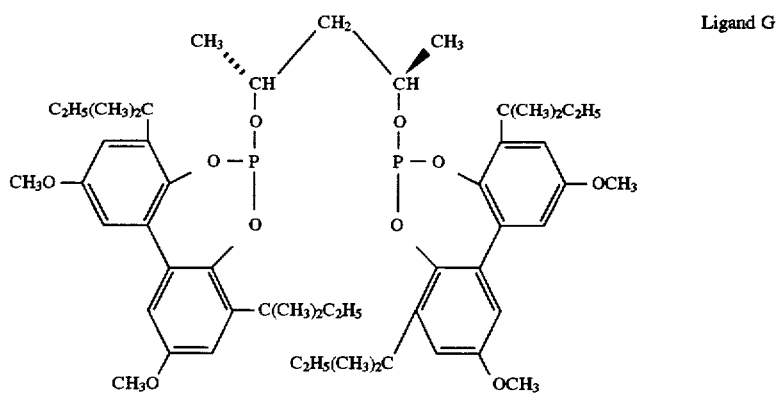
Ligand G

15

(2R,4R)-di[2,2'-(3,3'-di-tert-butyl-5,5'-dimethyl-1,1'-biphenyl)]-2,4-pentyldiphosphite having the formula:

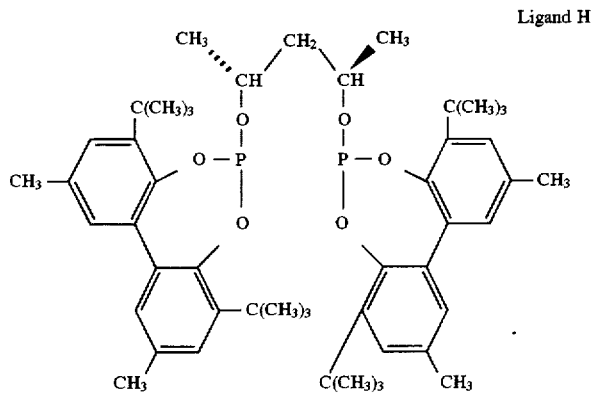

Ligand H

16

(2R,4R)-di[2,2'-(3,3'-di-tert-butyl-5,5'-dimethoxy-1,1'-biphenyl)]-2,4-pentyldiphosphite having the formula:

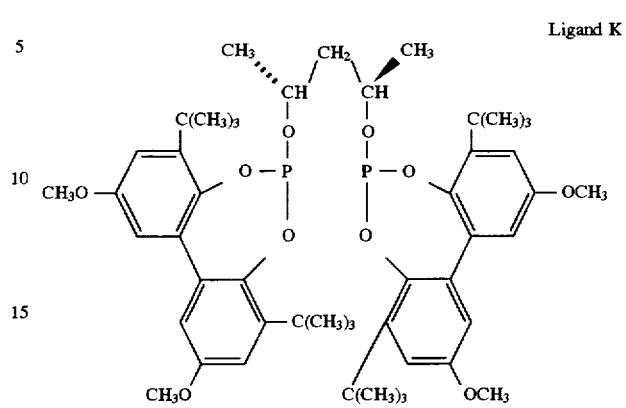

Ligand K (2R,4R)-di[2,2'-(3,3'-di-tert-butyl-5,5'-diethoxy-1,1'-biphenyl)]-2,4-pentyldiphosphite having the formula:

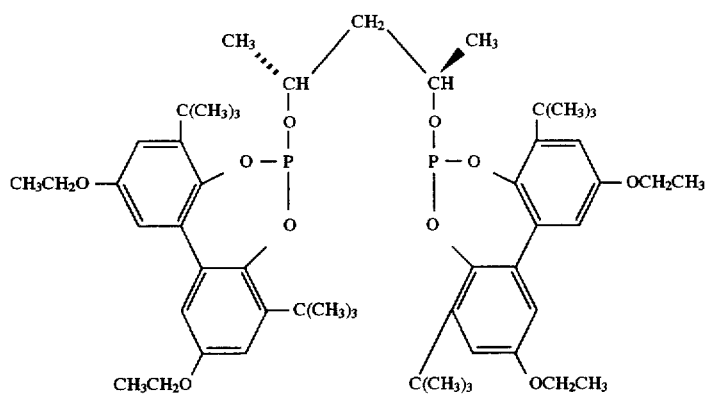

Ligand I (2R,4R)-di[2,2'-(3,3'-di-tert-butyl-5,5'-diethyl-1,1'-biphenyl)]-2,4-pentyldiphosphite having the formula:

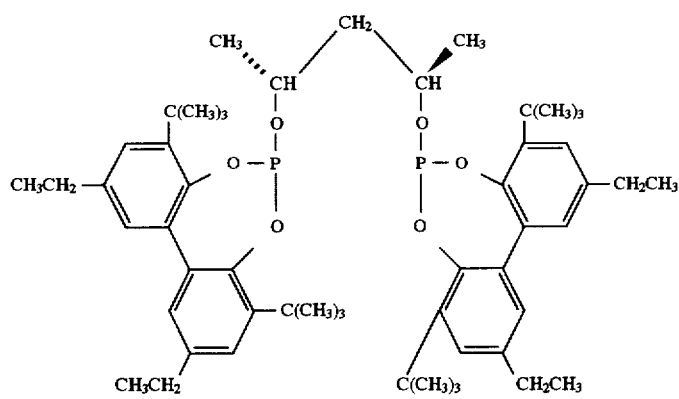

Ligand J

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

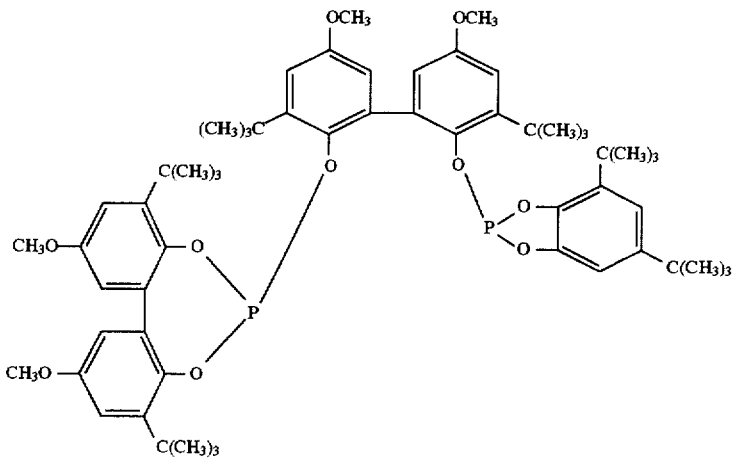
Ligand L
6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo [d,f][1,3,2]dioxaphosphepin having the formula:
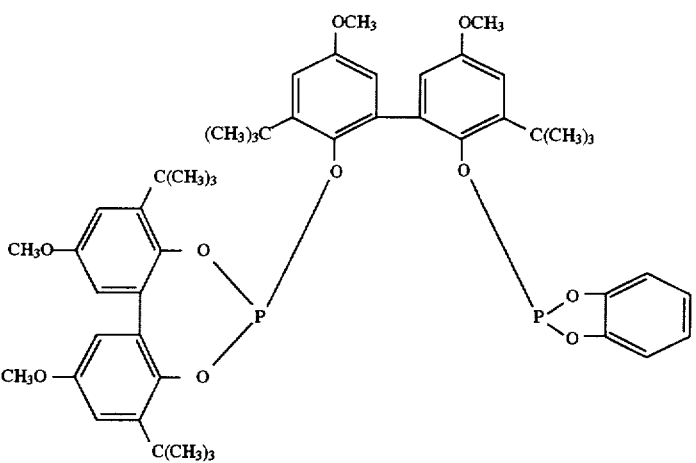
Ligand M
6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo [d,f][1,3,2]dioxaphosphepin having the formula:

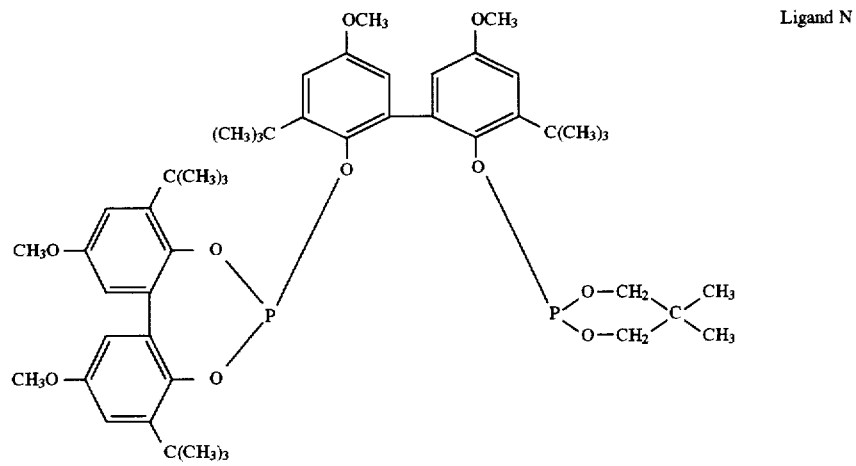

Ligand N

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, 6-(1,1-

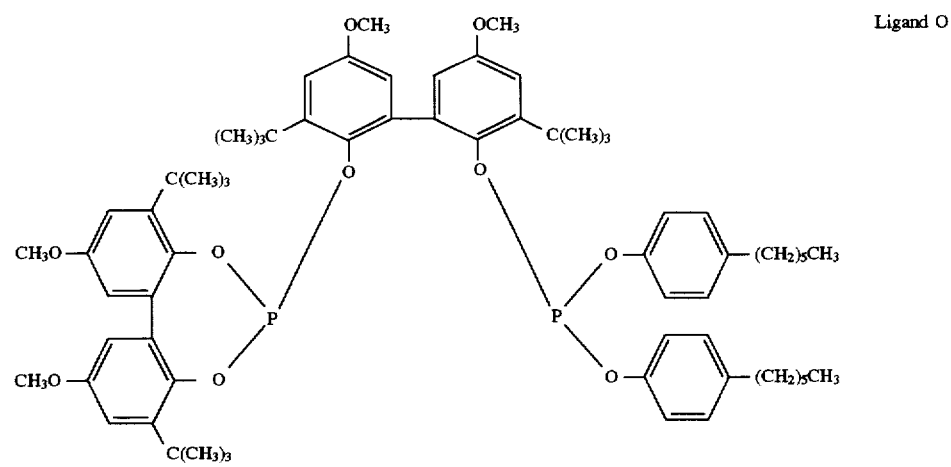

Ligand O dimethylethyl)phenyl diphenyl ester of phosphorous acid having the formula:

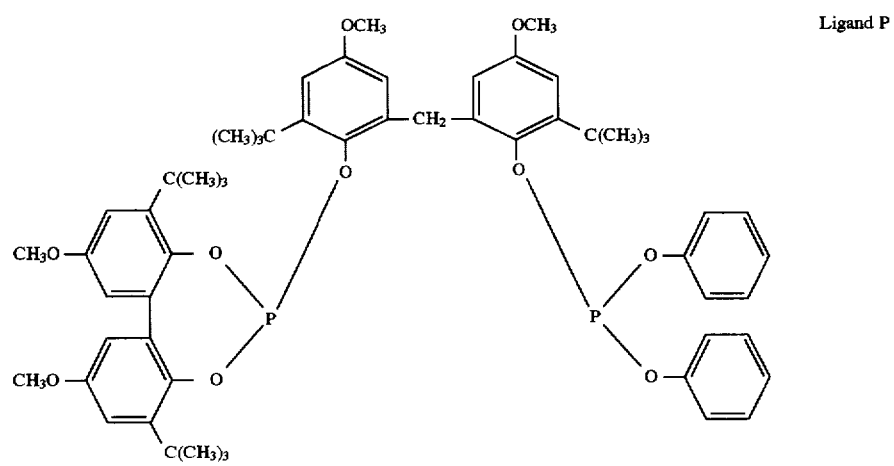

Ligand P 3-methoxy-1,3-cyclohexamethylene tetrakis[3,6-bis(1,1-dimethylethyl)-2-naphthalenyl]ester of phosphorous acid having the formula:

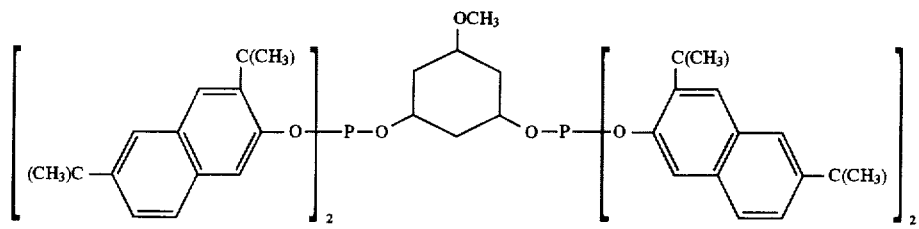

Ligand Q 2,5-bis(1,1-dimethylethyl)-1,4-phenylene tetrakis[2,4-bis(1,1-dimethylethyl)phenyl]ester of phosphorous acid having the formula:

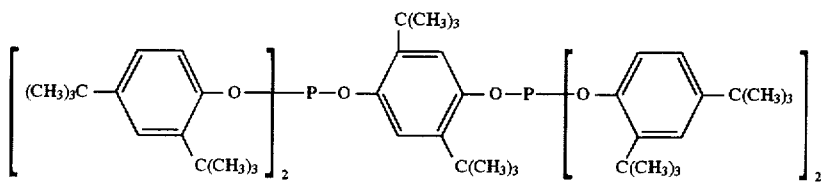

Ligand R methylenedi-2,1-phenylene tetrakis[2,4-bis(1,1-dimethylethyl)phenyl]ester of phosphorous acid having the formula:

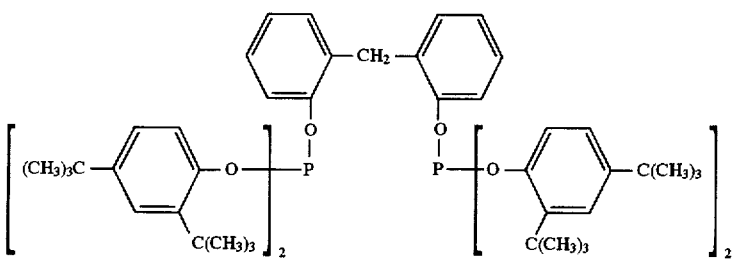

Ligand S

[1,1'-biphenyl]-2,2'-diyl tetrakis[2-(1,1-dimethylethyl)-4-methoxyphenyl]ester of phosphorous acid having the formula:

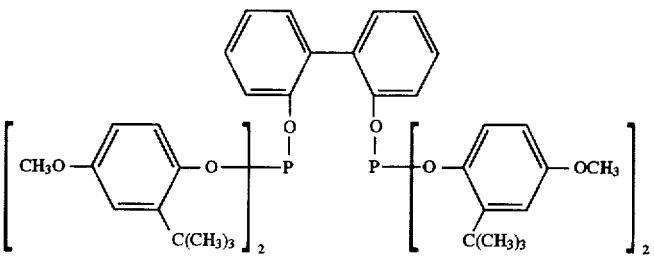

Ligand T

As noted above, the metal-organopolyphosphite ligand complex catalysts employable in this invention may be formed by methods known in the art. The metal-organopolyphosphite ligand complex catalysts may be in homogeneous or heterogeneous form. For instance, preformed rhodium hydrido-carbonyl-organopolyphosphite ligand catalysts may be prepared and introduced into the reaction mixture of a particular process. More preferably, the metal-organopolyphosphite ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organopolyphosphite ligand for the in situ formation of the active catalyst. In a preferred embodiment of this invention, rhodium dicarbonyl acetylacetonate is employed as a rhodium precursor and reacted in the presence of a solvent with the organopolyphosphite ligand to form a catalytic rhodium-organopolyphosphite ligand complex precursor which is introduced into the reaction zone along with excess (free) organopolyphosphite ligand for the in situ formation of the active catalyst. In any event, it is sufficient for the purpose of this invention that carbon monoxide, hydrogen and organopolyphosphite compound are all ligands that are capable of being complexed with the metal and that an active metal-organopolyphosphite ligand catalyst is present in the reaction mixture under the conditions used in the hydroformylation reaction.

More particularly, a catalyst precursor composition can be formed consisting essentially of a solubilized metal-organopolyphosphite ligand complex precursor catalyst, an organic solvent and free organopolyphosphite ligand. Such precursor compositions may be prepared by forming a solution of a rhodium starting material, such as a rhodium oxide, hydride, carbonyl or salt, e.g., a nitrate, which may or may not be in complex combination with a organopolyphosphite ligand as defined herein. Any suitable rhodium starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organopolyphosphite ligand rhodium carbonyl hydrides. Carbonyl and organopolyphosphite ligands, if not already complexed with the initial rhodium, may be complexed to the rhodium either prior to or in situ during the process.

By way of illustration, the preferred catalyst precursor composition of this invention consists essentially of a solubilized rhodium carbonyl organopolyphosphite ligand complex precursor catalyst, a solvent and optionally free organopolyphosphite ligand prepared by forming a solution of rhodium dicarbonyl acetylacetonate, an organic solvent and a organopolyphosphite ligand as defined herein. The organopolyphosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organopolyphosphite ligand complex precursor are soluble can be employed. The amounts of rhodium complex catalyst precursor, organic solvent and organopolyphosphite ligand, as well as their preferred embodiments present in such catalyst precursor compositions may obviously correspond to those amounts employable in the processes of this invention. Experience has shown that the acetylacetonate ligand of the precursor catalyst is replaced after the process, e.g., hydroformylation, has begun with a different ligand, e.g., hydrogen, carbon monoxide or organopolyphosphite ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor rhodium and hydroformylation start-up.

Accordingly, the metal-organopolyphosphite ligand complex catalysts used in the processes of this invention consists essentially of the metal complexed with carbon monoxide, i.e., hydroformylation, and an organopolyphosphite ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organopolyphosphite ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organopolyphosphite ligand complex catalyst may be present as a result of being ligands bound to a precursor catalyst and/or as a result of in situ formation, e.g., due to the hydrogen and carbon monoxide gases employed in hydroformylation process of this invention.

As noted above, the organopolyphosphite ligands can be employed as both the ligand of the metal-organopolyphosphite ligand complex catalyst, as well as, the free organopolyphosphite ligand that can be present in the reaction medium of the processes of this invention. In addition, it is to be understood that while the organopolyphosphite ligand of the metal-organopolyphosphite ligand complex catalyst and any excess free organopolyphosphite ligand preferably present in a given process of this invention are normally the same type of ligand, different types of organopolyphosphite ligands, as well as, mixtures of two or more different organopolyphosphite ligands may be employed for each purpose in any given process, if desired.

The amount of metal-organopolyphosphite ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organopolyphosphite ligand complex catalysts, the processes of this invention and especially the hydroformylation process can be carried out in the presence of free organopolyphosphite ligand. While the processes of this invention may be carried out in any excess amount of free organopolyphosphite ligand desired, the employment of free organopolyphosphite ligand may not be absolutely necessary. Accordingly, in general, amounts of ligand of from about 1.1 or less to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

As indicated above, the catalysts may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (i.e. alumina, silica, titania, or zirconia) carbon, or ion exchange resins. The catalyst may be supported on, or intercalated inside the pores of, a zeolite, glass or clay; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem. 1991, 403, 221–227; Nature, 1989, 339, 454–455; J. Catal. 1985, 96, 563–573; J. Mol. Cat. 1987, 39, 243–259.

The metal, e.g., rhodium, catalyst may be attached to a thin film or membrane support, such as cellulose acetate or polyphenylenesulfone, as described in for example J. Mol. Cat. 1990, 63, 213–221.

The metal, e.g., rhodium, catalyst may be attached to an insoluble polymeric support through an organophosphorus-containing ligand, such as a phosphite, incorporated into the polymer. The supported catalyst is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire process and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

More preferably, the hydroformylation reaction is carried out in the slurry phase due to the high boiling points of the products, and to avoid decomposition of the aldehyde products. The catalyst may then be separated from the product mixture, for example, by filtration or decantation. The reaction product fluid may contain a heterogeneous metal-organopolyphosphite ligand complex catalyst, e.g., slurry, or at least a portion of the reaction product fluid may contact a fixed heterogeneous metal-organopolyphosphite ligand complex catalyst during the particular process. In an embodiment of this invention, the metal-organopolyphosphite ligand complex catalyst may be slurried in the reaction product fluid.

This invention involves reducing the degradation or consumption of organopolyphosphite ligand, including adventitious hydrolysis, by reducing the concentration of free organopolyphosphite ligand present in the reaction product fluid below conventional levels. In a homogeneous process, e.g., hydroformylation, the organopolyphosphite ligand normally provides three functions. First, it coordinates with the metal, e.g., rhodium, and thereby influences the rate of hydroformylation. Secondly, through a combination of steric and electronic effects, it influences the ratio of linear to branched aldehyde. Finally, it stabilizes the metal, e.g., rhodium, against agglomeration to metal, e.g., rhodium metal. The latter function is particularly important when the reaction product fluid is sent to a vaporizer for separation of aldehyde product.

In conventional triphenylphosphine-modified metal system, it is not uncommon to have 100 to 200 moles of triphenylphosphine per mole of metal in order to achieve both a high linear to branched aldehyde ratio and to minimize catalyst deactivation reactions. Organopolyphosphite-modified metal catalysts can also be operated at relatively high ligand to metal ratios, e.g., from about 50 to about 100 moles of the organopolyphosphite ligand per mole of metal.

A disadvantage of the high organopolyphosphite ligand to metal, e.g., rhodium, ratios is the higher free organopolyphosphite ligand concentrations in solution. At a specified level of acidity and a specified water level, a consequence of the higher organopolyphosphite ligand concentration is a higher rate of hydrolysis of the desired organopolyphosphite ligand. This follows logically from the knowledge that hydrolysis is primarily a function of temperature, reaction product fluid acidity, water concentration and organopolyphosphite ligand concentration.

A difficult problem arises from the autocatalytic nature of the hydrolysis and the reaction zone residence time characteristics of, for example, a continuous stirred tank reactor (CSTR). The reaction product fluid has an specified average residence time in the reaction zone. The reaction product fluid is then removed from the reaction zone and/or the separation zone where a treatment to remove acidity, e.g., aqueous buffer treatment as described herein, and product removal can occur. At high organopolyphosphite ligand to rhodium ratios, the residence time needed to control reaction product fluid acidity below a threshold level, above which autocatalysis is severe, is shorter than the residence time required for olefin conversion and product removal. Operating the system at the residence time dictated by the increase in acidity could result in less than optimal raw material efficiencies. Operating the system at the residence time dictated by product removal can significantly increase the hydrolysis of the desired organopolyphosphite ligand.

In accordance with this invention, it has been discovered that organopolyphosphite ligands can be employed at very low organopolyphosphite ligand to metal ratios, e.g., as low as zero free moles of organopolyphosphite ligand per mole of metal, and achieve all three desirable benefits—rate, high linear to branched ratio and metal stabilization. By reducing the amount of free organopolyphosphite ligand to preferred levels of from zero to about 4 moles per mole of metal, adventitious hydrolysis can be reduced so that the process can be operated below the threshold for autocatalytic hydrolysis of organopolyphosphite ligand and can have a residence time in the reaction zone and/or separation zone sufficient to achieve high raw material efficiencies, e.g., high conversion of olefinic unsaturated compounds.

In a preferred embodiment, the hydroformylation processes of this invention are operated on a continuous basis at a free organopolyphosphite ligand concentration such that hydrolytic degradation of the organopolyphosphite ligand is less than about 1 gram, more preferably less than about 0.5 grams, and most preferably less than about 0.1 grams, of organopolyphosphite ligand per liter of reaction product fluid per day. The free organopolyphosphite ligand concentration is preferably from 0 to about 16 grams, more preferably from 0 to about 8 grams, and most preferably from 0 to about 1 gram, per liter of reaction product fluid.

As indicated above, the processes of this invention preferably operate at high raw material efficiencies, e.g., high conversion of olefinic unsaturated compounds. The raw material efficiency will be dependent on the reaction zone and/or separation zone residence time and, as indicated herein, the residence time will be dependent on controlling reaction product fluid acidity below a threshold level, above which autocatalysis is severe, and achieving desired olefin conversion and product removal. The processes of this invention may be operated at essentially complete raw material conversions. Gas and/or liquid recycle processes as described herein may be employed in order to achieve the desired high raw material efficiencies.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described. for example. in Kirk-Othmer. Encyclopedia of Chemical Technology, Fourth Edition. 1996. the pertinent portions of which are incorporated herein by reference. Depending on the particular process, operating temperatures may range from about —80° C. or less to about 500° C. or greater and operating pressures can range from about 1 psig or less to about 10,000 psig or greater.

The water concentration useful in this invention is not narrowly critical and can vary over a wide range. The hydroformylation processes may preferably be carried out in the presence of a minor amount of water, e.g., an amount ranging from about 0.05 to about 10 weight percent or higher if desired. based on the total weight of the reaction product fluid, and about preferably from about 0.05 to about 5 weight percent. Suitable water concentrations useful in this invention are disclosed in U.S. Pat. No. 5,288,918, the disclosure of which is incorporated herein by reference. The amount of water employed by the subject invention is sufficient to at least maintain the concentration of phosphorus acidic compounds below the threshold level that causes rapid degradation of the organopolyphosphite ligand. Preferably, the hydroformylation process is operated below the threshold for autocatalytic hydrolysis of organopolyphosphite ligand.

For instance, a preferred quantity of water is the quantity which ensures that any degradation of the organopolyphosphite ligand proceeds by the "non-catalytic mechanism" as described in "The Kinetic Rate Law for Autocatalytic Reactions" by Mata-Perez et al., Journal of Chemical Education, Vol. 64, No. 11, November 1987, pages 925 to 927, rather than by the "catalytic mechanism" described in said article. Typically maximum water concentrations are only governed by practical considerations.

It is to be understood that the preferred hydroformylation process of this invention is still considered to be essentially a "non-aqueous" process, which is to say, any water present in the hydroformylation reaction medium is not present in an amount sufficient to cause either the hydroformylation reaction or said medium to be considered as encompassing a separate aqueous or water phase or layer in addition to an organic phase.

The phosphorus acidic compound concentration in the hydroformylation processes of this invention is not narrowly critical and can vary over a wide range. The hydroformylation processes may preferably be carried out in the presence of a minor amount of one or more phosphorus acidic compounds, e.g., an amount ranging from about 1 part per million or less to about 1000 parts per million or greater if desired, and more preferably from about 1 part per million to about 200 parts per million, based on $H_3PO_4$. The concentration of phosphorus acidic compounds in the hydroformylation processes of this invention is preferably below the threshold level that causes rapid degradation of the organopolyphosphite ligand, i.e., below the threshold for autocatalytic hydrolysis of the organopolyphosphite ligand. The concentration of phosphorus acidic compounds in the hydroformylation processes of this invention is such that the pH of said reaction product fluid is from about 4 to about 9. The phosphorus acidic compound concentration is preferably controlled by employing an aqueous buffer solution as described herein.

The hydroformylation processes of this invention are conducted for a period of time sufficient to produce the desired products. The exact reaction zone residence time employed is dependent, in part, upon factors such as temperature, nature and proportion of starting materials, and the like. The reaction zone residence time will normally be within the range of from about one-half to about 200 hours or more, and preferably from less than about one to about 10 hours. The reaction zone residence time should be such that the hydroformylation process can be operated below the threshold for autocatalytic hydrolysis of organopolyphosphite ligand and have a residence time in the reaction zone sufficient to achieve high raw material efficiencies, e.g., high conversion of olefinic unsaturated compounds.

The processes of this invention and preferably the hydroformylation process may be conducted in the presence of an organic solvent for the metal-organopolyphosphite ligand complex catalyst. The solvent may also contain dissolved water up to the saturation limit. Depending on the particular catalyst and reactants employed, suitable organic solvents include, for example, alcohols, alkanes, alkenes, alkynes, ethers, aldehydes, ketones, esters, amides, amines, aromatics and the like. Any suitable solvent which does not unduly adversely interfere with the intended processes can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that amount sufficient to provide the reaction medium with the particular metal concentration desired for a given process. In general, the amount of solvent when employed may range from about 5 percent by weight up to about 99 percent by weight or more based on the total weight of the reaction mixture starting materials.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitrites. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The desired products of this invention may be recovered in any conventional manner and one or more separators or separation zones may be employed in any given process to recover the desired reaction product from its crude reaction product fluid. Suitable separation methods include, for example, solvent extraction, crystallization, distillation, vaporization, wiped film evaporation, falling film evaporation and the like. It may be desired to remove the products from the crude reaction mixture as they are formed through the use of trapping agents as described in published Pat. Cooperation Treaty Pat. Application WO 88/08835. A preferred method for separating the product mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discrete vessels. The at least one separation zone employed in this invention may be a single vessel or may comprise two or more discrete vessels. The at least one buffer treatment zone employed in this invention may be a single vessel or may comprise two or more discrete vessels. It should be understood that the reaction zone(s) and separation zone(s) employed herein may exist in the same vessel or in different vessels. For example, reactive separation techniques such as reactive distillation, reactive membrane separation and the like may occur in the reaction zone(s).

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes useful in this invention may be carried out in a multistaged reactor such as described, for example, in copending U.S. patent application Ser. No. 08/757,743, filed on an even date herewith, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

Hydroformylation Processes

A preferred process useful in this invention is hydroformylation. Illustrative metal-organopolyphosphite ligand complex catalyzed hydroformylation processes which may experience such hydrolytic degradation of the organopolyphosphite ligand and catalytic deactivation include such processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques of this invention may correspond to any known processing techniques. Preferred processes are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organopolyphosphite ligand complex catalyst in a liquid medium that also contains an organic solvent for the catalyst and ligand. Preferably free organopolyphosphite ligand is also present in the liquid hydroformylation reaction medium. By "free organopolyphosphite ligand" is meant organopolyphosphite ligand that is not complexed with (tied to or bound to) the metal, e.g., metal atom, of the complex catalyst. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194 and copending U.S. patent application Ser. No. 08/430,790, filed May 5, 1995, the disclosures of which are incorporated herein by reference, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syn gas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction product fluids employable herein includes any fluid derived from any corresponding hydroformylation process that contains at least some amount of four different main ingredients or components, i.e., the aldehyde product, a metal-organopolyphosphite ligand complex catalyst, free organopolyphosphite ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

The substituted or unsubstituted olefinic unsaturated starting material reactants that may be employed in the hydroformylation processes of this invention include both optically active (prochiral and chiral) and non-optically active (achiral) olefinic unsaturated compounds containing from 2 to 40, preferably 4 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U. S. Pat. Nos. 4,518,809 and 4,528,403). Moreover, such olefin compounds may further contain one or more ethylenic unsaturated groups, and of course, mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents which do not unduly adversely affect the hydroformylation process or the process of this invention such as described, for example, in U. S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 4 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Prochiral and chiral olefins useful in the asymmetric hydroformylation that can be employed to produce enantiomeric aldehyde mixtures that may be encompassed by in this invention include those represented by the formula:

(VIII)

wherein $R_1$, $R_2$, $R_3$ and $R_4$ are the same or different (provided $R^1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-organopolyphosphite ligand complex catalyst as described hereinabove. The hydroformylation catalysts may be in homogeneous or heterogeneous form during the reaction and/or during the product separation. Of course mixtures of such catalysts can also be employed if desired. The amount of metal-organopolyphosphite ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 350 parts per million of metal, e.g., rhodium.

In addition to the metal-organopolyphosphite ligand complex catalyst, free organopolyphosphite ligand (i.e., ligand that is not complexed with the metal) may also be present in the hydroformylation reaction medium. The free organopolyphosphite ligand may correspond to any of the above-defined organopolyphosphite ligands employable herein. It is preferred that the free organopolyphosphite ligand be the same as the organopolyphosphite ligand of the metal-organopolyphosphite ligand complex catalyst employed. However, such ligands need not be the same in any given process. The hydroformylation process of this invention may involve from about 0.1 moles or less to about 100 moles or higher, of free organopolypliosphite ligand per mole of metal in the hydroformylation reaction medium. Preferably the hydroformylation process of this invention is carried out in the presence of from about 1 to about 50 moles of organopolyphosphite ligand, and more preferably for organopolyphosphites from about 1.1 to about 4 moles of organopolyphosphite ligand, per mole of metal present in the reaction medium; said amounts of organopolyphosphite ligand being the sum of both the amount of organopolyphosphite ligand that is bound (complexed) to the metal present and the amount of free (non-complexed) organopolyphosphite ligand present. Since it is more preferred to produce non-optically active aldehydes by hydroformylating achiral olefins, the more preferred organopolyphosphite ligands are achiral type organopolyphosphite ligands, especially those encompassed by Formula (I) above, and more preferably those of Formulas (II) and (V) above. Of course, if desired, make-up or additional organopolyphosphite ligand can be supplied to the reaction medium of the hydroformylation process at any time and in any suitable manner, e.g. to maintain a predetermined level of free ligand in the reaction medium.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 500 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2CO$: molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about $-25°$ C to about $200°$ C. In general hydroformylation reaction temperatures of about $50°$ C. to about $120°$ C. are preferred for all types of olefinic starting materials. Of course it is to be understood that when non-optically active aldehyde products are desired, achiral type olefin starting materials and organopolyphosphite ligands are employed and when optically active aldehyde products are desired prochiral or chiral type olefin starting materials and organopolyphosphite ligands are employed. Of course, it is to be also understood that the hydroformylation reaction conditions employed will be governed by the type of aldehyde product desired.

The hydroformylation processes encompassed by this invention are also conducted in the presence of an organic solvent for the metal-organopolyphosphite ligand complex catalyst and free organopolyphosphite ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organopolyphosphite ligand complex catalyst, free organopolyphosphite ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-organopolyphosphite complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, phase separation, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Pat. Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction product fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reaction zone as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organopolyphosphite ligand and reaction products. When an alpha-mono-olefin reactant is also employed, the aldehyde derivative thereof can also be separated by the above methods.

More particularly, distillation and separation of the desired aldehyde product from the metal-organopolyphosphite complex catalyst containing reaction product fluid may take place at any suitable temperature desired. In general, it is recommended that such distillation take place at relatively low temperatures, such as below 150° C., and more preferably at a temperature in the range of from about 50° C. to about 140° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reaction zone to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

Acid Removal Treatment

As indicated above, the reaction product fluids containing phosphorus acidic compounds may be treated in an acid removal zone with an acid removal substance sufficient to remove at least some amount of the phosphorus acidic compounds from said reaction product fluid. Preferably, phosphorus acidic compounds can be removed from the reaction product fluid by (a) withdrawing from at least one reaction zone or at least one separation zone at least a portion of a reaction product fluid derived from a hydroformylation process and which also contains phosphorus acidic compounds formed during said hydroformylation process, (b) treating in at least one acid removal zone at least a portion of the withdrawn reaction product fluid derived from said hydroformylation process and which also contains phosphorus acidic compounds formed during said hydroformylation process with an acid removal substance sufficient to remove at least some amount of the phosphorus acidic compounds from said reaction product fluid, and (c) returning the treated reaction product fluid to at least one reaction zone or at least one separation zone.

In an embodiment of this invention, a means for preventing or minimizing ligand degradation and catalyst deactivation and/or precipitation that may be useful in this invention involves carrying out the invention described and taught in copending U.S. patent application Ser. Nos. (08/756,501) and (08/753,505), both filed on an even date herewith, the disclosures of which are incorporated herein by reference, which comprises using an aqueous buffer solution and optionally organic nitrogen compounds as disclosed therein.

For instance, said aqueous buffer solution invention comprises treating at least a portion of a metal-organopolyphosphite ligand complex catalyst containing reaction product fluid derived from said hydroformylation process and which also contains phosphorus acidic compounds formed during said hydroformylation process, with an aqueous buffer solution in order to neutralize and remove at least some amount of the phosphorus acidic compounds from said reaction product fluid, and then returning the treated reaction product fluid to the hydroformylation reaction zone or separation zone. Illustrative phosphorus acidic compounds include, for example, $H_3PO_3$, aldehyde acids such as hydroxy alkyl phosphonic acids, $H_3PO_4$ and the like. Said treatment of the metal-organopolyphosphite ligand complex catalyst containing reaction product fluid with the aqueous buffer solution may be conducted in any suitable manner or fashion desired that does not unduly adversely affect the basic hydroformylation process from which said reaction product fluid was derived.

Thus, for example, the aqueous buffer solution may be used to treat all or part of a reaction medium of a continuous liquid catalyst recycle hydroformylation process that has been removed from the reaction zone at any time prior to or after separation of the aldehyde product therefrom. More preferably said aqueous buffer treatment involves treating all or part of the reaction product fluid obtained after distillation of as much of the aldehyde product desired, e.g. prior to or during the recycling of said reaction product fluid to the reaction zone. For instance, a preferred mode would be to continuously pass all or part (e.g. a slip stream) of the recycled reaction product fluid that is being recycled to the reaction zone through a liquid extractor containing the aqueous buffer solution just before said catalyst containing residue is to re-enter the reaction zone.

Thus it is to be understood that the metal-organopolyphosphite ligand complex catalyst containing reaction product fluid to be treated with the aqueous buffer solution may contain in addition to the catalyst complex and its organic solvent, aldehyde product, free phosphite ligand, unreacted olefin, and any other ingredient or additive consistent with the reaction medium of the hydroformylation process from which said reaction product fluids are derived.

Typically maximum aqueous buffer solution concentrations are only governed by practical considerations. As noted, treatment conditions such as temperature, pressure and contact time may also vary greatly and any suitable combination of such conditions may be employed herein. In general liquid temperatures ranging from about 20° C. to about 80° C. and preferably from about 25° C., to about 60° C. should be suitable for most instances, although lower or higher temperatures could be employed if desired. Normally the treatment is carried out under pressures ranging from ambient to reaction pressures and the contact time may vary from a matter of seconds or minutes to a few hours or more.

Moreover, success in removing phosphorus acidic compounds from the reaction product fluid may be determined by measuring the rate degradation (consumption) of the organopolyphosphite ligand present in the hydroformylation reaction medium. In addition as the neutralization and extraction of phosphorus acidic compounds into the aqueous buffer solution proceeds, the pH of the buffer solution will decrease and become more and more acidic. When the buffer solution reaches an unacceptable acidity level it may simply be replaced with a new buffer solution.

The aqueous buffer solutions employable in this invention may comprise any suitable buffer mixture containing salts of oxyacids, the nature and proportions of which in the mixture, are such that the pH of their aqueous solutions may range from 3 to 9, preferably from 4 to 8 and more preferably from 4.5 to 7.5. In this context suitable buffer systems may include mixtures of anions selected from the group consisting of phosphate, carbonate, citrate and borate compounds and cations selected from the group consisting of ammonium and alkali metals, e.g. sodium, potassium and the like. Such buffer systems and/or methods for their preparation are well known in the art.

Preferred buffer systems are phosphate buffers and citrate buffers, e.g. monobasic phosphate/dibasic phosphates of an alkali metal and citrates of an alkali metal. More preferred are buffer systems consisting of mixtures of the monobasic phosphate and the dibasic phosphate of sodium or potassium.

Optionally, an organic nitrogen compound may be added to the hydroformylation reaction product fluid to scavenge the acidic hydrolysis byproducts formed upon hydrolysis of the organophosphite ligand, as taught, for example, in U.S. Pat. No. 4,567,306. Such organic nitrogen compounds may be used to react with and to neutralize the acidic compounds by forming conversion product salts therewith, thereby preventing the rhodium from complexing with the acidic hydrolysis byproducts and thus helping to protect the activity of the metal, e.g., rhodium, catalyst while it is present in the reaction zone under hydroformylation conditions. The choice of the organic nitrogen compound for this function is, in part, dictated by the desirability of using a basic material that is soluble in the reaction medium and does not tend to catalyze the formation of aldols and other condensation products at a significant rate or to unduly react with the product aldehyde.

Such organic nitrogen compounds may contain from 2 to 30 carbon atoms, and preferably from 2 to 24 carbon atoms. Primary amines should be excluded from use as said organic nitrogen compounds. Preferred organic nitrogen compounds should have a distribution coefficient that favors solubility in the organic phase. In general more preferred organic nitrogen compounds useful for scavenging the phosphorus acidic compounds present in the hydroformylation reaction product fluid of this invention include those having a pKa value within ±3 of the pH of the aqueous buffer solution employed. Most preferably the pKa value of the organic nitrogen compound will be essentially about the same as the pH of the aqueous buffer solution employed. Of course it is to be understood that while it may be preferred to employ only one such organic nitrogen compound at a time in any given hydroformylation process, if desired, mixtures of two or more different organic nitrogen compounds may also be employed in any given processes.

Illustrative organic nitrogen compounds include e.g., trialkylamines, such as triethylamine, tri-n-propylamine, tri-n-butylamine, tri-iso-butylamine, tri-iso-propylamine, tri-n-hexylamine, tri-n-octylamine, dimethyl-iso-propylamine, dimethyl-hexadecylamine, methyl-di-n-octylamine, and the like, as well as substituted derivatives thereof containing one or more noninterfering substituents such as hydroxy groups, for example triethanolamine, N-methyl-di-ethanolamine, tris-(3-hydroxypropyl)-amine, and the like. Heterocyclic amines can also be used such as pyridine, picolines, lutidines, collidines, N-methylpiperidine, N-methylmorpholine, N-2'-hydroxyethylmorpholine, quinoline, iso-quinoline, quinoxaline, acridien, quinuclidine, as well as, diazoles, triazole, diazine and triazine compounds, and the like. Also suitable for possible use are aromatic tertiary amines, such as N,N-dimethylaniline, N,N-diethylaniline, N,N-dimethyl-p-toluidine, N-methyldiphenylamine, N,N-dimethylbenzylamine, N,N-dimethyl-1-naphthylamine, and the like. Compounds containing two or more amino groups, such as N,N,N',N'-tetramethylethylene diamine and triethylene diamine (i.e. 1,4-diazabicyclo-[2.2.2]-octane) can also be mentioned.

Preferred organic nitrogen compounds useful for scavenging the phosphorus acidic compounds present in the hydroformylation reaction product fluids of the this invention are heterocyclic compounds selected from the group consisting of diazoles, triazoles, diazines and triazines, such as those disclosed and employed in copending U.S. patent application Ser. No. (08/756,789), filed on an even date herewith, the disclosure of which is incorporated herein by reference. For example, benzimidazole and benztriazole are preferred candidates for such use.

Illustrative of suitable organic nitrogen compounds include those permissible organic nitrogen compounds described in Kirk-Othmer, Encyclopedia of Chemical Technology, Fourth Edition, 1996, the pertinent portions of which are incorporated herein by reference.

The amount of organic nitrogen compound that may be present in the reaction product fluid for scavenging the phosphorus acidic compounds present in the hydroformylation reaction product fluids of the this invention is typically sufficient to provide a concentration of at least about 0.0001 moles of free organic nitrogen compound per liter of reaction product fluid. In general the ratio of organic nitrogen compound to total organophosphite ligand (whether bound with rhodium or present as free organophosphite) is at least about 0.1:1 and even more preferably at least about 0.5:1. The upper limit on the amount of organic nitrogen compound employed is governed mainly only by economical considerations. Organic nitrogen compound: organophosphite molar ratios of at least about 1:1 up to about 5:1 should be sufficient for most purpose.

It is to be understood the organic nitrogen compound employed to scavenge said phosphorus acidic compounds need not be the same as the heterocyclic nitrogen compound employed to protect the metal catalyst under harsh conditions such as exist in the aldehyde vaporizer-separator, as taught in copending U.S. patent application Ser. No. 08/756, 789, referred to above. However, if said organic nitrogen compound and said heterocyclic nitrogen compound are desired to be the same and perform both said functions in a given process, care should be taken to see that there will be a sufficient amount of the heterocyclic nitrogen compound present in the reaction medium to also provide that amount of free heterocyclic nitrogen compound in the hydroformylation process, e.g., vaporizer-separator, that will allow both desired functions to be achieved.

Accordingly the aqueous buffer solution treatment of this invention will not only remove free phosphoric acidic compounds from the metal-organophosphite ligand complex catalyst containing reaction product fluids, the aqueous buffer solution also surprisingly removes the phosphorus acidic material of the conversion product salt formed by the use of the organic nitrogen compound scavenger when employed, i.e., the phosphorus acid of said conversion product salt remains behind in the aqueous buffer solution, while the treated reaction product fluid, along with the reactivated (free) organic nitrogen compound is returned to the hydroformylation reaction zone.

Another problem that has been observed when organopolyphosphite ligand promoted metal catalysts are employed in hydroformylation processes, e.g., continuous liquid catalyst recycle hydroformylation processes, that involve harsh conditions such as recovery of the aldehyde via a vaporizer-separator, i.e., the slow loss in catalytic activity of the catalysts is believed due at least in part to the harsh conditions such as exist in a vaporizer employed in the separation and recovery of the aldehyde product from its reaction product fluid. For instance, it has been found that when an organopolyphosphite promoted rhodium catalyst is placed under harsh conditions such as high temperature and low carbon monoxide partial pressure, that the catalyst deactivates at an accelerated pace with time, due most likely to the formation of an inactive or less active rhodium species, which may also be susceptible to precipitation under prolonged exposure to such harsh conditions. Such evidence is also consistent with the view that the active catalyst which under hydroformylation conditions is believed to comprise a complex of rhodium, organopolyphosphite, carbon monoxide and hydrogen, loses at least some of its coordinated carbon monoxide ligand during exposure to such harsh conditions as encountered in vaporization, which provides a route for the formation of catalytically inactive or less active rhodium species. The means for preventing or minimizing such catalyst deactivation and/or precipitation involves carrying out the invention described and taught in copending U.S. patent application Ser. No. (08/756,789), referred to above, which comprises carrying out the hydroformylation process under conditions of low carbon monoxide partial pressure in the presence of a free heterocyclic nitrogen compound as disclosed therein.

By way of further explanation it is believed the free heterocyclic nitrogen compound serves as a replacement ligand for the lost carbon monoxide ligand thereby forming a neutral intermediate metal species comprising a complex of the metal, organopolyphosphite, the heterocyclic nitrogen compound and hydrogen during such harsh conditions, e.g., vaporization separation, thereby preventing or minimizing the formation of any such above mentioned catalytic inactive or less active metal species. It is further theorized that the maintenance of catalytic activity, or the minimization of its deactivation, throughout the course of such continuous liquid recycle hydroformylation is due to regeneration of the active catalyst from said neutral intermediate metal species in the reactor (i.e. hydroformylation reaction zone) of the particular hydroformylation process involved. It is believed that under the higher syn gas pressure hydroformylation conditions in the reactor, the active catalyst complex comprising metal, e.g., rhodium, organopolyphosphite, carbon monoxide and hydrogen is regenerated as a result of some of the carbon monoxide in the reactant syn gas replacing the heterocyclic nitrogen ligand of the recycled neutral intermediate rhodium species. That is to say, carbon monoxide having a stronger ligand affinity for rhodium, replaces the more weakly bonded heterocyclic nitrogen ligand of the recycled neutral intermediate rhodium species that was formed during vaporization separation as mentioned above, thereby reforming the active catalyst in the hydroformylation reaction zone.

Thus the possibility of metal catalyst deactivation due to such harsh conditions is said to be minimized or prevented by carrying out such distillation of the desired aldehyde product from the metal-organopolyphosphite catalyst containing reaction product fluids in the added presence of a free heterocyclic nitrogen compound having a five or six membered heterocyclic ring consisting of 2 to 5 carbon atoms and from 2 to 3 nitrogen atoms, at least one of said nitrogen atoms containing a double bond. Such free heterocyclic nitrogen compounds may be selected from the class consisting of diazole, triazole, diazine, and triazine compounds, such as, e.g., benzimidazole or benzotriazole, and the like. The term "free" as it applies to said heterocyclic nitrogen compounds is employed therein to exclude any acid salts of such heterocyclic nitrogen compounds, i.e., salt compounds formed by the reaction of any phosphorus acidic compound present in the hydroformylation reaction product fluids with such free heterocyclic nitrogen compounds as discussed herein above.

It is to be understood that while it may be preferred to employ only one free heterocyclic nitrogen compound at a time in any given hydroformylation process, if desired, mixtures of two or more different free heterocyclic nitrogen compounds may also be employed in any given process. Moreover the amount of such free heterocyclic nitrogen compounds present during harsh conditions, e.g., the vaporization procedure, need only be that minimum amount necessary to furnish the basis for at least some minimization of such catalyst deactivation as might be found to occur as a result of carrying out an identical metal catalyzed liquid recycle hydroformylation process under essentially the same conditions, in the absence of any free heterocyclic nitrogen compound during vaporization separation of the aldehyde product. Amounts of such free heterocyclic nitrogen compounds ranging from about 0.01 up to about 10 weight percent, or higher if desired, based on the total weight of the hydroformylation reaction product fluid to be distilled should be sufficient for most purposes.

An alternate method of transferring acidity from the hydroformylation reaction product fluid to an aqueous fraction is through the intermediate use of a heterocyclic amine which has a fluorocarbon or silicone side chain of sufficient size that it is immiscible in both the hydroformylation reaction product fluid and in the aqueous fraction. The heterocyclic amine may first be contacted with the hydroformylation reaction product fluid where the acidity present in the reaction product fluid will be transferred to the nitrogen of the heterocyclic amine. This heterocyclic amine layer may then be decanted or otherwise separated from the reaction product fluid before contacting it with the aqueous fraction where it again would exist as a separate phase. The heterocyclic amine layer may then be returned to contact the hydroformylation reaction product fluid.

Another means for preventing or minimizing ligand degradation and catalyst deactivation and/or precipitation that may be useful in this invention involves carrying out the invention described and taught in copending U.S. patent application Ser. Nos. (08/753,504) and (08/753,503), both filed on an even date herewith, the disclosures of which are incorporated herein by reference, which comprises using water and optionally organic nitrogen compounds as disclosed therein.

For instance, it has been found that hydrolytic decomposition and rhodium catalyst deactivation as discussed herein can be prevented or lessened by treating at least a portion of the reaction product fluid derived from the hydroformylation process and which also contains phosphorus acidic compounds formed during the hydroformylation process with water sufficient to remove at least some amount of the phosphorus acidic compounds from the reaction product fluid. Although both water and acid are factors in the hydrolysis of organophosphite ligands, it has been surprisingly discovered that hydroformylation reaction systems are more tolerant of higher levels of water than higher levels of acid. Thus, the water can surprisingly be used to remove acid and decrease the rate of loss of organophosphite ligand by hydrolysis.

Yet another means for preventing or minimizing ligand degradation and catalyst deactivation and/or precipitation that may be useful in this invention involves carrying out the invention described and taught in copending U.S. patent application Ser. Nos. (D-17652) and (08/756,786), both filed on an even date herewith, the disclosures of which are incorporated herein by reference, which comprises using water in conjunction with acid removal substances and optionally organic nitrogen compounds as disclosed therein.

For instance, it has been found that hydrolytic decomposition and rhodium catalyst deactivation as discussed herein can be prevented or lessened by treating at least a portion of the reaction product fluid derived from the hydroformylation process and which also contains phosphorus acidic compounds formed during said hydroformylation process with water in conjunction with one or more acid removal substances, e.g., oxides, hydroxides, carbonates, bicarbonates and carboxylates of Group 2, 11 and 12 metals, sufficient to remove at least some amount of the phosphorus acidic compounds from said reaction product fluid. Because metal salt contaminants, e.g., iron, zinc, calcium salts and the like, in a hydroformylation reaction product fluid undesirably promote the self condensation of aldehydes, an advantage is that one can use the acidity removing capability of certain acid removal substances with minimal transfer of metal salts to the hydroformylation reaction product fluid.

A further means for preventing or minimizing ligand degradation and catalyst deactivation and/or precipitation that may be useful in this invention involves carrying out the invention described and taught in copending U.S. patent application Ser. Nos. (08/756,482) and (08/756,788), both filed on an even date herewith, the disclosures of which are incorporated herein by reference, which comprises using ion exchange resins and optionally organic nitrogen compounds as disclosed therein.

For instance, it has been found that hydrolytic decomposition and rhodium catalyst deactivation as discussed herein can be prevented or lessened by (a) treating in at least one scrubber zone at least a portion of said reaction product fluid derived from said hydroformylation process and which also contains phosphorus acidic compounds formed during said hydroformylation process with water sufficient to remove at least some amount of the phosphorus acidic compounds from said reaction product fluid and (b) treating in at least one ion exchange zone at least a portion of the water which contains phosphorus acidic compounds removed from said reaction product fluid with one or more ion exchange resins sufficient to remove at least some amount of the phosphorus acidic compounds from said water. Because passing a hydroformylation reaction product fluid directly through an ion exchange resin can cause rhodium precipitation on the ion exchange resin surface and pores, thereby causing process complications, an advantage is that one can use the acidity removing capability of ion exchange resins with essentially no loss of rhodium.

Other means for removing phosphorus acidic compounds from the reaction product fluids of this invention may be employed if desired. This invention is not intended to be limited in any manner by the permissible means for removing phosphorus acidic compounds from the reaction product fluids.

The processes of this invention may involve reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst, to produce one or more products, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, enables a reaction rate of at least 25 percent of the reaction rate enabled by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, enables a normal:branched product isomer ratio lower than the normal:branched product isomer ratio enabled by the organopolyphosphite ligand of said metal-organopolyphosphite ligand complex catalyst. See, for example, copending U.S. patent application Ser. Nos. (08/756,500) and (08/756,741), both filed on an even date herewith, the disclosures of which are incorporated herein by reference.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

EXAMPLES 1–17

In a continuous catalyst liquid recycle manner, a mixed olefin starting material of butene-1 and butene-2 (cis and trans) was hydroformylated. The liquid recycle reactor system employed contained from one to three one-liter stainless steel stirred tank reactors, combined in series, each containing a vertically mounted agitator and a circular tubular sparger near the bottom of the reactor for feeding the olefin and/or syn gas. The sparger contained a plurality of holes of sufficient size to provide the desired gas flow into the liquid body. The reactors were jacketed with a silicone oil shell as means of bringing the contents of the reactors up to reaction temperature. All reactors contained internal cooling coils for controlling the reaction temperature. The reactors were connected via a line to transfer any unreacted gases to the subsequent reactor and were further connected via a line so that a portion of the liquid reaction solution containing aldehyde product and catalyst from an upstream reactor could be purged into the subsequent reactor wherein unreacted olefin from the previous reactor can be further hydroformylated. Each reactor also contained a pneumatic liquid level controller for automatic control of the liquid levels in the reactors. The first reactor further contained a line for introducing the olefin and syn gas through the sparger, while make up syn gas was added to subsequent reactors via the same transfer line carrying the unreacted gases from the previous reactor. The final reactor in the series also contained a blow-off vent for removal of the unreacted gases. A line from the bottom of the final reactor was connected to the top of a vaporizer so that a portion of the liquid reaction solution could be pumped from the final reactor to the vaporizer. Vaporized aldehyde was disengaged from the non-volatile components of the liquid reaction solution in the gas-liquid separator part of the vaporizer. In some instances, unreacted olefin was stripped from the liquid catalyst product or the condensed aldehyde product and returned to the first reactor in the series.

The hydroformylation reaction was conducted by charging about 1 liter of a catalyst precursor solution of rhodium dicarbonyl acetylacetonate sufficient to achieve about 300 to 100 ppm rhodium in the operating reactor solution, about 1.0 weight percent of Ligand D (as identified herein) (about 3 mole equivalents of ligand per mole of rhodium), and the balance being C5 aldehyde and another heavier solvent (C5 trimer, Texanol®, or tetraglyme) to each reactor. The reactor system was then purged with nitrogen to remove any oxygen present. Then about 100 psig nitrogen pressure was put on both reactors and the reactors heated to their reaction temperatures given in Table A below. Controlled flows of purified hydrogen, carbon monoxide and a mixed olefin starting material of butene-1 and butene-2 (cis and trans) were fed through the sparger into the bottom of reactor 1 and the reactor pressures increased to achieve the partial pressures given in Table A. As the liquid level in a reactor started to increase as a result of liquid aldehyde product formation a portion of the liquid reaction solution of the reactor was pumped into the subsequent reactor at a rate sufficient to maintain a constant liquid level in the reactor. If the reactor was the final reactor in the series, a portion of the liquid reaction solution was pumped to the vaporizer/separator at a rate sufficient to maintain a constant liquid level in that reactor. Blow-off gas from the final reactor was analyzed and measured. A controlled flow of make-up syn gas (CO and H2) was added to the reactors in order to maintain their desired partial pressure in those reactors. The operating pressures and reaction temperatures were maintained throughout the hydroformylation. The liquid reaction product solution from the final reactor was subjected to an increased temperature and decreased pressure sufficient to vaporize the aldehyde product from the liquid reaction solution. Typical conditions required for the separation were from 90° C. to 115° C. and from 20 to 2 psia. The vaporized product was condensed and collected in a product receiver. The remaining non-volatilized catalyst containing liquid reaction solution was pumped to vessel means to contact the solution with the aqueous buffer identified in Table A. Experiments where either 1,2-Epoxydodecane or 3,4-Epoxycyclohexylmethyl 3,4-epoxycyclohexanecarboxylate resin was used were not treated with the aqueous buffer solution, but pumped directly back to the first reactor in series.

A C5 aldehyde catalyst solution containing 240 parts per million of rhodium, 6 grams/liter of Ligand D, 1,2-epoxydodecane (0.6 grams) was added on the third day and each subsequent third day of the run. The catalyst solution throughout was contacted with carbon monoxide, hydrogen, and mixed butenes at partial pressures of 84, 89 and 41 psi, respectively all at a reactor temperature of 85° C. The product was removed continuously by means of an external vaporizer. Ligand D concentration was determined/monitored by $^{31}$P NMR. An average ligand usage rate of 0.1 grams/liter/day was observed (Example 1 in Table A). Other runs were conducted in a similar manner and the results are given in Table A (Examples 2–7).

A C5 aldehyde catalyst solution containing 240 parts per million of rhodium and 6 grams/liter of Ligand D was contacted with carbon monoxide, hydrogen, and mixed butenes at partial pressures of 40, 39 and 24 psi, respectively all at a reactor temperature of 75° C. The product was removed continuously by means of external vaporizer and the concentrated catalyst solution passed through a 0.1M pH7 aqueous $Na_2HPO_4/NaH_2PO_4$ buffer solution prior to returning the concentrated catalyst to the hydroformylation reactor. Ligand D concentration was determined/monitored by $^{31}$p NMR. An average ligand usage rate of 0.34 grams/liter/day was observed (Table A—Example 15). Experiments 8–17 in Table A were all run under nominally the same conditions except the "topped-up" Ligand D concentration was varied throughout the run.

TABLE A

| | Acid | React. Temp | Partial Pressures, psi | | | Initial [L] | Usage Rate |
|---|---|---|---|---|---|---|---|
| Ex. | Control | °C. | CO | $H_2$ | $C_4H_8$ | G/L | G/L/Day |
| 1 | DDE[a] | 85 | 84 | 89 | 41 | 6 | 0.10 |
| 2 | ERL-4221[b] | 85 | 90 | 90 | 49 | 4.2 | 0.07 |
| 3 | DDE[a] | 85 | 74 | 77 | 55 | 6 | 0.12 |

TABLE A-continued

| | Acid | React. Temp | Partial Pressures, psi | | | Initial [L] | Usage Rate |
|---|---|---|---|---|---|---|---|
| Ex. | Control | °C. | CO | $H_2$ | $C_4H_8$ | G/L | G/L/Day |
| 4 | DDE[a] | 85 | 89 | 97 | 30 | 8 | 0.09 |
| 5 | DDE[a] | 85 | 84 | 88 | 38 | 6 | 0.11 |
| 6 | DDE[a] | 75 | 38 | 30 | 32 | 6 | 0.08 |
| 7 | DDE[a] | 75 | 40 | 37 | 16 | 6 | 0.1 |
| 8 | Extractor[c] | 75 | 40 | 39 | 24 | 4 | 0.37 |
| 9 | Extractor[c] | 75 | 40 | 39 | 24 | 2 | 0.27 |
| 10 | Extractor[c] | 75 | 40 | 39 | 24 | 3 | 0.13 |
| 11 | Extractor[c] | 75 | 40 | 39 | 24 | 5 | 0.37 |
| 12 | Extractor[c] | 75 | 40 | 39 | 24 | 1.67 | 0.1 |
| 13 | Extractor[c] | 75 | 40 | 39 | 24 | 2 | 0.13 |
| 14 | Extractor[c] | 75 | 40 | 39. | 24 | 0.67 | 0.13 |
| 15 | Extractor[c] | 75 | 40 | 39 | 24 | 6 | 0.34 |
| 16 | Extractor[c] | 75 | 40 | 39 | 24 | 2 | 0.29 |
| 17 | Extractor[c] | 75 | 40 | 39 | 24 | 2 | 0.11 |

[a]1,2-Epoxydodecane
[b]3,4-Epoxycyclohexylmethyl 3,4-epoxycyclohexanecarboxylate resin
[c]An 0.1M aqueous pH7 $Na_2HPO_4/NaH_2PO_4$ buffer solution FIG. 1 is a graphical representation of free ligand concentration (grams/liter) versus average ligand usage (grams/liter/day) based on the experimental data set out in Table A above.

Examples 18 to 22 illustrate the in situ buffering effect of nitrogen containing additives such as benzimidazole and the ability of these additives to transfer the acidity to an aqueous buffer solution.

EXAMPLE 18

This control example illustrates the stability of Ligand D (as identified herein) in a solution containing 200 parts per million of rhodium, and 0.39 percent by weight of Ligand D in butyraldehyde containing aldehyde dimer and trimer in the absence of added acid or benzimidazole.

To a clean, dry 25 milliliter vial was added 12 grams of the butyraldehyde solution mentioned above. Samples were analyzed for Ligand D using High Performance Liquid Chromatography after 24 and 72 hours. The weight percent of Ligand D was determined by High Performance Liquid Chromatography relative to a calibration curve. No change in the concentration of Ligand D was observed after either 24 or 72 hours.

EXAMPLE 19

This Example is similar to Example 18 except that phosphorus acid was added to simulate the type of acid that might be formed during hydrolysis of an organophosphite.

The procedure for Example 18 was repeated with the modification of adding 0.017 grams of phosphorous acid ($H_3PO_3$) to the 12 gram solution. After 24 hours the concentration of Ligand D had decreased from 0.39 to 0.12 percent by weight; after 72 hours the concentration of Ligand D had decreased to 0.04 percent by weight. This data shows that strong acids catalyze the decomposition of Ligand D.

EXAMPLE 20

This Example is similar to Example 18 except that both phosphorus acid and benzimidazole were added.

The procedure for Example 18 was repeated with the modification of adding 0.018 grams of phosphorous acid and 0.0337 grams of benzimidazole to the solution. No decomposition of Ligand D was observed after either 24 or 72 hours. This shows that the addition of benzimidazole effectively buffers the effect of the strong acid and thereby prevents the rapid decomposition of Ligand D.

EXAMPLE 21

This example shows that an aqueous buffer can recover the acidity from the nitrogen base in situ buffer and allow the nitrogen base to partition into the organic phase, where it can be recycled to the hydroformylation zone.

Solid (benzimidazole)($H_3PO_4$) was prepared by placing 1.18 grams (10 mmole) of benzimidazole in a 250 milliliter beaker and dissolving the benzimidazole in 30 milliliters of tetrahydrofuran. To this solution was slowly added 0.5 grams of 86 percent by weight of phosphoric acid ($H_3PO_4$). Upon addition of the acid a precipitate formed. The precipitate was collected on a sintered glass frit and washed with tetrahydrofuran. The resulting solid was air-dried with the application of vacuum and used without any further purification. 0.109 grams (0.504 mmole) of the water-soluble (benzimidazole)($H_3PO_4$) solid prepared in the previous step was dissolved in 10 grams of 0.1M pH 7 sodium phosphate buffer solution. The resulting solution was extracted with 10 grams of valeraldehyde. The organic layer was then separated from the aqueous layer using a separatory funnel. The volatile components were then removed from the organic layer by distillation at 100° C. to yield a solid. The solid was identical to authentic benzimidazole as shown by thin layer chromatography utilizing a 1:1 by volume mixture of chloroform and acetone as the eluent and silica as the stationary phase. Based on recovery of the solid, benzimidazole was completely transferred to the organic phase.

This data shows that an organic soluble nitrogen base which exists as a strong acid salt can be regenerated by contact with an aqueous buffer and returned to the organic phase.

EXAMPLE 22

This example shows that a buffer solution is effective at neutralizing an organic soluble salt of a weak base and strong acid thus allowing the base to return to the organic phase and effectively removing the acid from the organic phase.

A butyraldehyde solution was prepared containing 1.0 percent by weight of benzotriazole. The solution was then analyzed by Gas Chromatography for benzotriazole content to serve as a reference sample. To the solution prepared in the previous step was added 0.25 mole equivalents of phosphorous acid ($H_3PO_3$). In a one pint glass bottle was added 50 grams of the butyraldehyde solution containing benzotriazole and 50 grams of a pH 7, 0.2 molar sodium phosphate buffer solution. The mixture was stirred for 15 minutes and then transferred to a separatory funnel. The aqueous layer was then separated from the aldehyde layer. The aqueous layer was analyzed for $H_3PO_3$ content by Ion Chromatography. The aldehyde layer was analyzed for benzotriazole content by Gas Chromatography and $H_3PO_3$ content by Ion Chromatography. The $H_3PO_3$ was found to be completely transferred into the aqueous layer. Complete return of benzotriazole to the butyraldehyde layer was also found.

This data shows that an organic soluble salt of a weak base and strong acid can be completely neutralized by contacting the organic phase with an aqueous buffer solution and that the free base is thereby returned to the organic phase.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process which comprises reacting one or more reactants in the presence of a metal-organopolyphosphite ligand complex catalyst to produce a reaction product fluid comprising one or more products, wherein said process is conducted at a free organopolyphosphite ligand concentration of from 0 to about 8 grams per liter of reaction product fluid; and treating at least a portion of said reaction product fluid which also contains phosphorus acidic compounds formed during said process with an acid removal substance sufficient to remove at least some amount of the phosphorus acidic compounds from said reaction product fluid.

2. A process which comprises reacting one or more reactants in the presence of a metal-organopolyphosphite ligand complex catalyst to produce a reaction product fluid comprising one or more products, wherein said process is conducted (a) at a free organopolyphosphite ligand concentration of from 0 to about 8 grams per liter of reaction product fluid and (b) at a reaction zone and/or separator zone residence time sufficient to prevent and/or lessen hydrolytic degradation of the organopolyphosphite ligand and deactivation of the metal-organopolyphosphite ligand complex catalyst; and treating at least a portion of said reaction product fluid which also contains phosphorus acidic compounds formed during said process with an acid removal substance sufficient to remove at least some amount of the phosphorus acidic compounds from said reaction product fluid.

3. An improved process for producing one or more products which comprises (i) reacting in at least one reaction zone one or more reactants in the presence of a metal-organopolyphosphite ligand complex catalyst to produce a reaction product fluid comprising one or more products and (ii) separating in at least one separation zone or in said at least one reaction zone the one or more products from said reaction product fluid, the improvement comprising preventing and/or lessening hydrolytic degradation of the organopolyphosphite ligand and deactivation of the metal-organopolyphosphite ligand complex catalyst by conducting said process (a) at a free organopolyphosphite ligand concentration of from 0 to about 8 grams per liter of reaction product fluid, and (b) at a reaction zone and/or separator zone residence time sufficient to prevent and/or lessen hydrolytic degradation of the organopolyphosphite ligand and deactivation of the metal-organopolyphosphite ligand complex catalyst; and by treating in at least one acid removal zone at least a portion of said reaction product fluid derived from said process and which also contains phosphorus acidic compounds formed during said process with an acid removal substance sufficient to remove at least some amount of the phosphorus acidic compounds from said reaction product fluid.

4. An improved process for producing one or more products which comprises (i) reacting in at least one reaction zone one or more reactants in the presence of a metal-organopolyphosphite ligand complex catalyst to produce a reaction product fluid comprising one or more products and (ii) separating in at least one separation zone or in said at least one reaction zone the one or more products from said reaction product fluid, the improvement comprising preventing and/or lessening hydrolytic degradation of the organopolyphosphite ligand and deactivation of the metal-organopolyphosphite ligand complex catalyst by conducting said process (a) at a free organopolyphosphite ligand concentration of from 0 to about 8 grams per liter of reaction product fluid, and (b) at a reaction zone and/or separator zone residence time sufficient to prevent and/or lessen hydrolytic degradation of the organopolyphosphite ligand and deactivation of the metal-organopolyphosphite ligand complex catalyst; and by removing phosphorus acidic compounds from said reaction product fluid derived from said process by (a) withdrawing from said at least one reaction zone or said at least one separation zone at least a portion of a reaction product fluid derived from said process and which also contains phosphorus acidic compounds formed during said process, (b) treating in at least one acid removal zone at least a portion of the withdrawn reaction product fluid derived from said process and which also contains phosphorus acidic compounds formed during said process with an acid removal substance sufficient to remove at least some amount of the phosphorus acidic compounds from said reaction product fluid, and (c) returning the treated reaction product fluid to said at least one reaction zone or said at least one separation zone.

5. The process of claim 1 which comprises a hydroformylation, hydroacylation (intramolecular and intermolecular), hydrocyanation, hydroamidation, hydroesterification, aminolysis, alcoholysis, carbonylation, isomerization or transfer hydrogenation process.

6. The process of claim 1 wherein the free organopolyphosphite ligand concentration is from about 0.1 moles or less to about 4 moles of organopolyphosphite ligand per mole of metal.

7. The process of claim 1 wherein the free organopolyphosphite ligand concentration is such that said process can be operated below the threshold for autocatalytic hydrolysis of the organopolyphosphite ligand.

8. The process of claim 1 wherein said metal-organopolyphosphite ligand complex catalyst is homogeneous or heterogeneous.

9. The process of claim 1 wherein said reaction product fluid contains a homogeneous or heterogeneous metal-organopolyphosphite ligand complex catalyst or at least a portion of said reaction product fluid contacts a fixed heterogeneous metal-organopolyphosphite ligand complex catalyst during said hydroformylation process.

10. The process of claim 1 wherein said metal-organopolyphosphite ligand complex catalyst comprises rhodium complexed with an organopolyphosphite ligand represented by the formula:

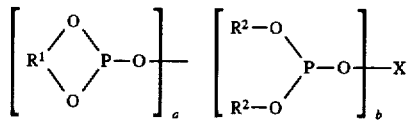

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, wherein a and b can be the same or different and each have a value of 0 to 6, with the proviso that the sum of a+b is 2 to 6 and n equals a+b.

11. The process of claim 10 wherein said metal-organopolyphosphite ligand complex catalyst comprises rhodium complexed with an organopolyphosphite ligand having the formula selected from:

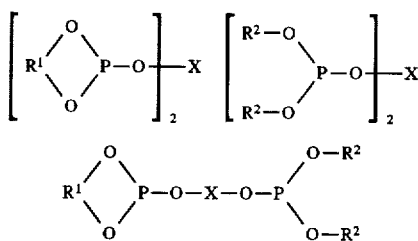

wherein X represents a substituted or unsubstituted divalent hydrocarbon bridging radical containing from 2 to 40 carbon atoms, each $R^1$ is the same or different and represents a divalent hydrocarbon radical containing from 4 to 40 carbon atoms, and each $R^2$ is the same or different and represents a substituted or unsubstituted monovalent hydrocarbon radical containing from 1 to 24 carbon atoms.

12. The process of claim 10 wherein said metal-organopolyphosphite ligand complex catalyst comprises rhodium complexed with an organopolyphosphite ligand having the formula selected from:

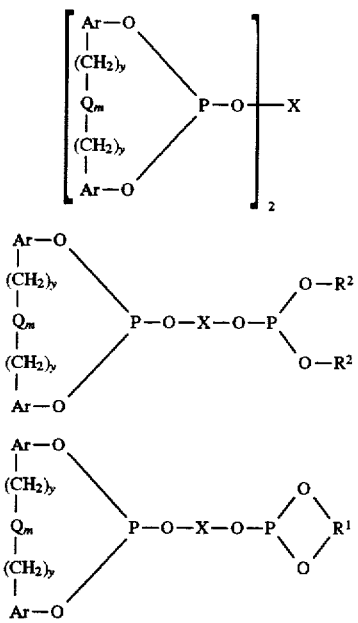

wherein X represents a substituted or unsubstituted divalent hydrocarbon bridging radical containing from 2 to 40 carbon atoms, $R^1$ is a divalent hydrocarbon radical containing from 4 to 40 carbon atoms, each $R^2$ is the same or different and represents a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —C($R^3$)$_2$—, —O—, —S—, —$NR^4$—, $Si(R^5)_2$— and —CO—, wherein each $R^3$ is the same or different and represents hydrogen, alkyl radicals having from 1 to 12 carbon atoms, phenyl, tolyl, and anisyl, $R^4$ represents hydrogen or a methyl radical, each $R^5$ is the same or different and represents hydrogen or a methyl radical, and m is a value of 0 or 1.

13. The process of claim 1 wherein said free organopolyphosphite ligand is represented by the formula:

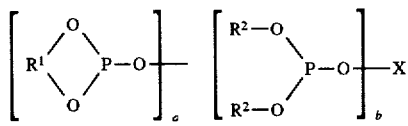

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, wherein a and b can be the same or different and each have a value of 0 to 6, with the proviso that the sum of a+b is 2 to 6 and n equals a+b.

14. The process of claim 13 wherein said free organopolyphosphite ligand is represented by the formula:

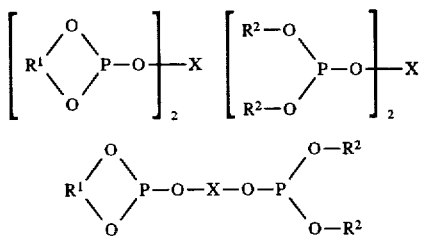

wherein X represents a substituted or unsubstituted divalent hydrocarbon bridging radical containing from 2 to 40 carbon atoms, each $R^1$ is the same or different and represents a divalent hydrocarbon radical containing from 4 to 40 carbon atoms, and each $R^2$ is the same or different and represents a substituted or unsubstituted monovalent hydrocarbon radical containing from 1 to 24 carbon atoms.

15. The process of claim 13 wherein said free organopolyphosphite ligand is represented by the formula:

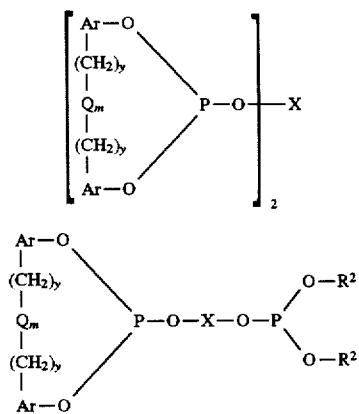

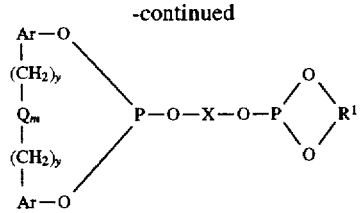

wherein X represents a substituted or unsubstituted divalent hydrocarbon bridging radical containing from 2 to 40 carbon atoms, $R^1$ is a divalent hydrocarbon radical containing from 4 to 40 carbon atoms, each $R^2$ is the same or different and represents a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —$C(R^3)_2$—, —O—, —S—, —$NR^4$—, $Si(R^5)_2$— and —CO—, wherein each $R^3$ is the same or different and represents hydrogen, alkyl radicals having from 1 to 12 carbon atoms, phenyl, tolyl, and anisyl, $R^4$ represents hydrogen or a methyl radical, each $R^5$ is the same or different and represents hydrogen or a methyl radical, and m is a value of 0 or 1.

16. The process of claim 1 wherein the reaction product fluid containing phosphorus acidic compounds is treated with an aqueous buffer solution, water, ion exchange resin or a Group 2, 11 or 12 metal oxide, hydroxide, carbonate, bicarbonate or carboxylate.

17. The process of claim 16 wherein phosphorus acidic compounds present in the reaction product fluid are scavenged by an organic nitrogen compound that is also present in said reaction product fluid and wherein at least some amount of the phosphorus acidic compound of the conversion products of the reaction between said phosphorus acidic compound and said organic nitrogen compound are also neutralized and removed by the treatment with the aqueous buffer solution, water, ion exchange resin or a Group 2, 11 or 12 metal oxide, hydroxide, carbonate, bicarbonate or carboxylate.

18. The process of claim 17 wherein the organic nitrogen compound is selected from the group consisting of diazoles, triazoles, diazines and triazines.

19. The process of claim 18 wherein the organic nitrogen compound is benzimidazole or benzotriazole.

* * * * *